US 010183032B2

(12) United States Patent
McDowell et al.

(10) Patent No.: US 10,183,032 B2
(45) Date of Patent: *Jan. 22, 2019

(54) METHODS FOR TREATING BACTERIAL INFECTION

(71) Applicants: Ball State Innovation Corporation, Muncie, IN (US); STC.UNM, Albuquerque, NM (US)

(72) Inventors: Susan A. McDowell, Yorktown, IN (US); Robert E. Sammelson, Muncie, IN (US); Larry A. Sklar, Albuquerque, NM (US); Mark K. Haynes, Albuquerque, NM (US)

(73) Assignees: Ball State Innovation Corporation, Muncie, IN (US); STC.UNM, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/691,977

(22) Filed: Aug. 31, 2017

(65) Prior Publication Data

US 2018/0021357 A1 Jan. 25, 2018

Related U.S. Application Data

(63) Continuation-in-part of application No. 14/561,787, filed on Dec. 5, 2014, now Pat. No. 9,763,967, which is a continuation-in-part of application No. 13/773,871, filed on Feb. 22, 2013, now Pat. No. 9,259,415.

(60) Provisional application No. 61/912,723, filed on Dec. 6, 2013, provisional application No. 61/671,054, filed on Jul. 12, 2012, provisional application No. 61/644,798, filed on May 9, 2012, provisional application No. 61/601,807, filed on Feb. 22, 2012.

(51) Int. Cl.
*A61K 31/415* (2006.01)
*A61K 31/63* (2006.01)
*A61K 31/635* (2006.01)

(52) U.S. Cl.
CPC ................................ *A61K 31/635* (2013.01)

(58) Field of Classification Search
None
See application file for complete search history.

(56) References Cited

U.S. PATENT DOCUMENTS

2007/0066651 A1 3/2007 Cuberes Altisen et al.
2013/0345277 A1 12/2013 Wandinger-Ness et al.

OTHER PUBLICATIONS

Wilding, E.I., et al., Essentiality, expression and characterization of the class ii 3-hydroxy-3methylglutaryl coenzyme A reductase of *Staphylococcus aureus*. J. Bacteriol 182(18):5147-52. Jan. 1, 2000.
Jerwood, S., et al. Unexpected antimicrobial effect of statins. J. Antimicrob Chemother 61(2):362-4. Jan. 1, 2008.
Lopez, D., et al., Functional microdomains in bacterial membranes. Genes & Development 24(17):1893-902. Jan. 1, 2010.
Singh, R., et al., Enhanced production of exopolysaccharide matrix and biofilm by a menadione-auxotrophic *Staphylococcus aureus* small-colony variant. Journal of Medical Microbiology 59(Pt 5):521-7. Jan. 1, 2010.
Que, Y.A., et al., Infective endocarditis. Nat Rev Cardiol 8(6):322-36. Jan. 1, 2011.
Secor, P.R., et al., *Staphylococcus aureus* Biofilm and Planktonic cultures differentially impact gene expression, mapk phosphorylation, and cytokine production in human keratinocytes. BMC Microbiology 11:143. Jan. 1, 2011.
Vanhaesebroeck, B., et al., Signaling by distinct classes of phosphoinositide 3-kinases. Exp Cell Res 253(1):239-54 Jan. 1, 1999.
Cantley, L.C., The Phosphoiositide 3-kinase pathway. Science 296(5573)1655-7. Jan. 1, 2002.
Jimenez, C., et al., Role of the PI3K regulatory subunit in the control of actin organization and cell migration. J Cell Biol 151(2):249-62. Jan. 1, 2000.
Kim do, Y., et al., Design and biological evaluation of novel tubulin inhibitors as antimitotic agents using a pharmacophore binding model with tubulin. Journal of Medicinal Chemistry 49(19):5664-70. Jan. 1, 2006.
Bashir, R., et al., Synthesis of some new 1,3,5-trisubstituted pyrazolines bearing benzene sulfonamide as anticancer and anti-inflammatory agents. Bioorganic & Medicinal Chemistry Letters 21(14):4301-5. Jan. 1, 2011.
Soliman, R., Preparation and antidiabetic activity of some sulfonylurea derivatives of 3,5-disubstituted pyrazoles. Journal of Medicinal Chemistry 22(3):321-5. Jan. 1, 1979.
Yan, Q., et al., Inhibitory effects of 5-benzylidene barbituate derivatives on mushroom tyrosinase and their antibacterial activities. European Journal of Medicinal Chemistry 44(10):4235-43. Jan. 1, 2009.
Knop, K., et al., Poly(ethylene glycol) in drug delivery: pros and cons as well as potential alternatives. Angew Chem Int Ed Engl 49(36):6288-308. Jan. 1, 2010.
Gajbhiye, V., et al., Pharmaceutical and biomedical potential of PEGylated dendrimers. Curr Pharm Design 13(4):415-29. Jan. 1, 2007.
Seedher, N., et al., Solubility enhancement of Cox-2 inhibitors using various solvent systems, AAPS PharmSciTech. 4 (2003) E33. Jan. 1, 2003.
Klein, I.K., et al., Intersectin-2L regulates caveola endocytosis secondary to CDC42—mediated actin polymerization. J. Biol. Chem 248:25953-25961. Jan. 1, 2009.
David, M.Z., et al., Community-associated methicillin-resistant *Staphylococcus aureus*: epidemiology and clinical consequences of an emerging epidemic. Clinical Microbiology Reviews 23(3):616-87. Jan. 1, 2010.

(Continued)

*Primary Examiner* — Bong-Sook Baek
(74) *Attorney, Agent, or Firm* — Daniel L. Boots; Brian W. Chellgren; Bingham Greenebaum Doll LLP

(57) ABSTRACT

The present disclosure relates to molecules that function as selective modulators (i.e., inhibitors and agonists) of the Ras-homologous (Rho) family of small GTPases and, in particular, CDC42 GTPase, and their use to treat bacterial infection including systemic infection from sources such as *Staphylococcus aureus* and *Streptococcus pyogenes*.

16 Claims, 31 Drawing Sheets

(56) References Cited

OTHER PUBLICATIONS

Furuya, E.Y., et al., Antimicrobial strategies for the prevention and treatment of cardiovascular infections. Current Opinion in Pharmacology 3(5):464-9. Jan. 1, 2003.
Darouiche, R.O., Treatment of infections associated with surgical implants. N Engl J Med 350(14):1422-9. Jan. 1, 2004.
Lowy, R.D., *Staphylococcus aureus* infections. N Engl J Med 339(8):520-32. Jan. 1, 1998.
Otto, M., Looking toward basic science for potential drug discovery targets against community-associated MRSA. Medicinal Research Reviews 30(1):1-22. Jan. 1, 2010.
Liappis, A.P., et al., The effect of statins on mortality in patients with bacteremia. Clin Infect Dis 33(8):1352-7. Jan. 1, 2001.
Almog, Y., et al., Prior statin therapy is associated with a decreased rate of severe sepsis. Circulation 110(7):880-5. Jan. 1, 2004.
Yasuda, H., et al., Simvastatin improves sepsis-induced mortality and acute kidney injury via renal vascular effects. Kidney Int 69(9):1535-42. Jan. 1, 2006.
Spitzer, A.L., et al., Statins attenuate sepsis. Surgery 139(3):283-7. Jan. 1, 2006.
Kruger, P., et al., Statin therapy is associated with fewer deaths in patients with bacteremia. Intensive Care Med 32(1):75-9. Jan. 1, 2006.
Kruger, S., et al. Nonuse of statins—a new risk factor for infectious death in cardiovascular patients? Crit Care Med 35(2):631-2. Jan. 1, 2007.
Terblanche, M., et al., Statins and sepsis: multiple modifications at multiple levels. Lancet Infect Dis 7(5):358-68. Jan. 1, 2007.
Dobesh, P.P., et al., Reduction in mortality associated with statin therapy in patients with severe sepsis. Pharmacotherapy 29(6):621-30. Jan. 1, 2009.
Donnino, M.W., et al., Statin therapy is associated with decreased mortality in patients with infection. Acad Emerg Med 16(3):230-4 Jan. 1, 2009.
Horn, M.P., et al., Simvastatin inhibits *Staphylococcus aureus* host cell invasion through modulation of isoprenoid intermediates. J Pharmacol Exp Ther 326(1):135-43. Jan. 1, 2008.
Chow, O.A., et al., Statins enhance formation of phagocyte extracellular traps. Cell Host Microbe 8(5):445-54. Jan. 1, 2010.
McDowell, S.A., et al., Simvastatin is protective during *Staphylococcus aureus* pneumonia. Current Pharmaceutical Biotechnology 12:1455-62. Jan. 1, 2011.
Mahboobi, S.K. et al., Systemic infections can decrease the threshold of statin-induced muscle injury. South Med J 99(4):403-4. Jan. 1, 2006.
Vincent, A., et al., Statins for sepsis: a cautionery note. Intensive Care Med 32(5):795. Jan. 1, 2006.
Drage, S.M., et al., Statins and sepsis: panacea or Pandora's box? Lancet Infect Dis 7(2):80; author reply 80-1. Jan. 1, 2007.
Golomb, B.A., et al., Statin adverse effects: a review of the literature and evidence for a mitochondrial mechanism. Am J Cardiovasc Drugs 8(6):373-418. Jan. 1, 2008.
Brealey, D.A., et al., Potential metabolic consequences of statins in sepsis. Crit Care Med 39(6):1514-20. Jan. 1, 2011.
Fessler, M.B., Simvastatin as a potential therapeutic for acute respiratory distress syndrome. Am J Respir Crit Care Med 180(10):1031; author reply 1031-2. Jan. 1, 2009.
Surviladze, Z.A., et al., A Potent and Selective Inhibitor of CDC42 GTPase. Jan. 1, 2010.
Endo, A., The discovery and development of HMG-CoA reductase inhibitors. J Lipid Res 33(11):1569-82 Jan. 1, 1992.
Stankiewicz, T.E., et al., GTPase activating protein function of p85 facilitates uptake and recycling of the beta1 integrin. Biochem Biophys Res Commun 391(1):443-8. Jan. 1, 2010.
Sinensky, M., Recent advances in the study of prenylated proteins. Biochem Biophys Acta 1484(2-3):93-106. Jan. 1, 2000.
Edwards, A.M., et al., How does *Staphylococcus aureus* escape the bloodstream? Trends in Microbiology 19(4):184-90. Jan. 1, 2011.

Agarwal, V., et al., CDC42 and the phosphatidylinositol 3-kinase-Akt pathway are essential for PspC-mediated internalization of pheumococci by respiratory epithelial cells. J Biol Chem 284(29):19427-36. Jan. 1, 2009.
Van den Broeke, C., et al., An emerging role for p21-activated kinases (Paks) in viral infections. Trends Cell Biol 20 (3)160-9. Jan. 1, 2010.
Sinha, B., et al., Is *Staphylococcus aureus* an intracellular pathogen? Trends Microbiol 8(8):343-4. Jan. 1, 2000.
Garzoni, C., et al., *Staphylococcus aureus*: new evidence for intracellular persistence. Trends Microbiol 17(2):59-65. Jan. 1, 2009.
Proctor, R.A., et al., Variant subpopulations of *Staphylococcus aureus* as cause of persistent and recurrent infections. Infect Agents Dis 3(6):302-12. Jan. 1, 1994.
Menzies, B.E., et al., Internalization of *Staphylococcus aureus* by endothelial cells induces apoptosis. Infect Immun 66(12):5994-8. Jan. 1, 1998.
Lowy, F.D., Is *Staphylococcus aureus* an intracellular pathogen? Trends Microbiol 8(8):341-3. Jan. 1, 2000.
Sinha, B., et al., Mechanism and consequences of invasion of endothelial cells by *Staphylococcus aureus*. Thromb Haemost 94(2)266-77. Jan. 1, 2005.
Foster, T.J., Immune evasion by *Staphylococci*. Nat Rev Microbiol 3(12):948-58. Jan. 1, 2005.
Que, Y.A. et al., Fibrinogen and fibronectin binding cooperate for valve infection and invasion in *Staphylococcus aureus* experimental endocarditis. J Exp Med 201(10):1627-35. Jan. 1, 2005.
Hauck, C.R., et al., Sticky connections: extracellular matrix protein recognition and integrin-mediated cellular invasion by *Staphylococcus aureus*. Curr Opin Microbiol 9(1):5-11. Jan. 1, 2006.
Sendi, P., et al., Staphylococcus aureus as an intracellular pathogen: the role of small colony variants. Trends in Microbiology 17(2):54-8. Jan. 1, 2009.
Bokoch, G.M., Regulation of innate immunity by Tho GTPases. Trends Cell Biol 15(3):163-71. Jan. 1, 2005.
Costerton, J.W., et al., Bacterial biofilms: a common cause of persistent infections. Science 284(5418):1318-22. Jan. 1, 1999.
Otto, M., Staphylococcal biofilms. Current Topics in Microbiology and Immunology 322:207-28. Jan. 1, 2008.
Brady, R.A., et al., Osteomyelitis and the role of biofilms in chronic infection. FEMS Immunology and Medicinal Microbiology 52(1):13-22. Jan. 1, 2008.
Feid-Allah, H.M., Trisubstituted pyrazoles of possible antidiabetic and antibacterial activity. Pharmazie 36:754-6. Jan. 1, 1981.
Johnson, D.I., CDC42: An essential Rho-type GTPase controlling eukaryotic cell polarity. Microbiol Mol Biol Rev 63(1):54-105. Jan. 1, 1999.
Tuchscherr, L., et al., *Staphylococcus aureus* phenotype switching: an effective bacterial strategy to escape host immune response and establish a chronic infection. EMBO Mol Med 3(3):129-41. Jan. 1, 2011.
Chorianpoulos, E., et al., The role of endothelial cell biology in endocarditis. Cell & Tissue Research 335(1):153-63. Jan. 1, 2009.
Zheng Y. et al., Activation of phosphoinositide 3-kinase activity by CDC42Hs binding to p85. J Biol Chem 269 (29):18727-30. Jan. 1, 1994.
Friesen, J.A., et al., The 3-hydroxy-3-methylglutaryl coenzyme-A (HMG-CoA) reductases. Genome Biol 5(11):248. Jan. 1, 2004.
Soong et al. J Biol. Chem., 286: 35891-35898 Jan. 1, 2011.
Stevens, Joanne M., et al., Actin-dependent movement of bacterial pathogens. Nature Reviews-Microbiology, vol. 4, Feb. 2006, 91-101. Jan. 1, 2006.
Wiedemann, Agnes, et al., Yersinia enterocolitica invasin triggers phagocytosis via b1 integrins, CDC42Hs and WASp in macrophages, Cellular Microbiology (2001) 3(10), 693-702. Mar. 10, 2001.
Scott, Cameron C., et al., Phosphatidylinositol-4,5-bisphosphate hydrolysis directs actin remodeling during phagocytosis, J Cell Biol, vol. 169, No. 1, Apr. 11, 2005, 139-149. Apr. 4, 2005.
Osiak Anna-Eleonor, et al., Subconfluent endothelial cells form podosomes downstream of cytokine and RhoGTPase signaling, Experimental Cell Research, 307 (2005) 342-353. May 13, 2005.
DeMali, Kris A., et al., Integrin signaling to the actin cytoskeleton, Current Opinion in Cell Biology, 2003, 15:572-582. Jan. 1, 2003.

(56) References Cited

OTHER PUBLICATIONS

Katsumi, Akira, et al., Integrins in Mechanotransduction, J Biol Chem, vol. 279, No. 13, Mar. 26, 2004, 12001-12004. Feb. 11, 2004.
May, Robin C., et al., Phagocytosis and the actin cytoskeleton, J Cell Science 114, 1061-1077. Jan. 1, 2017.
Isberg, Ralph R., et al., Signaling and invasin-promoted uptake via integrin receptors, Microbes and Infection, 2, 2000, 793-801. Jan. 1, 2000.
Cordero, Diana, et al., Small Molecule Inhibitors Limit Endothelial Cell Invasion by *Staphylococcus aureus*, Current Pharmaceutical Biotechnology, 2014, 15, vol. 9, 1-11. Jan. 1, 2014.
Schroder, Andreas, et al., *Staphylococcus aureus* Fibronectin Binding Protein-A Induces Motile Attachment Sites and Complex Actin Remodeling in Living Endothelial Cells, Molecular Biology of the Cell, vol. 17, Dec. 2006, 5198-5210. Dec. 1, 2006.
Nobes, Catherine D., et al., Rho, Rac, and Cdc42 GTPases Regulate the Assembly of Multimolecular Focal Complexes Associated with Actin Stress Fibers, lamellipodia, and Filopodia, Cell, vol. 81, Apr. 7, 1995, 53-62. Apr. 7, 1995.
Nagahama, Ryo, et al., Rho GTPase protein Cdc42 is critical for postnatal cartilage development, Biochemical and Biophysical Research Communications, 2016, 813-817. Oct. 10, 2016.
Schwartz, Martin Alexander, et al., An activated Rac mutant functions as a dominant negative for membrane ruffling, Oncogene, 17, 1998, 625-629. Jan. 1, 1998.
Zhou, Xuan, et al., Cell Type-specific Signaling Function of RhoA GTPase: Lessons from Mouse Gene Targeting, J Biol Chem, vol. 288, No. 51, Dec. 20, 2013, 36179-36188. Dec. 20, 2013.
Patel, Jayesh, et al., Differential activation and function of Rho GTPases during Salmonella-host cell interactions, J Cell Biol, vol. 175, No. 3, Nov. 6, 2006, 453-463. Nov. 6, 2006.
Chen, Li-Mei, et al., Requirement of CDC42 for Salmonella-Induced Cytoskeletal and Nuclear Responses, Science, vol. 274, Dec. 20, 1996, 2115-2118. Dec. 20, 1996.
Lee, Keunwook, et al., Cdc42 Promotes Host Defenses against Fatal Infection, Infection and Immunity, vol. 81, No. 8, Aug. 2013, 2714-2723. Aug. 1, 2013.
Melendez, Jaime, et al., Signaling Role of Cdc42 in Regulating Mammalian Physiology, J Biol Chem, vol. 286, No. 4, Jan. 28, 2011, 2375-2381. Jan. 28, 2011.
Cerione, Richard A., Cdc42: new roads to travel, Trends in Cell Biology, vol. 14, No. 3, Mar. 2004, 127-132. Mar. 1, 2004.
Tapon, Nicolas, et al., Rho, Rac and Cdc42 GTPases regulate the organization of the actin cytoskeleton, Current Opinion in Cell Biology, 1997, vol. 9, 86-92. Jan. 1, 1997.
Collier, Michael A., et. al., Delivery of host cell-directed therapeutics for intracellular pathogen clearance, Expert Rev Anti Infect Ther., Nov. 2013, 11 (11), 1225-1235. Nov. 1, 2013.
Kerrigan, Steven W., et al., Dysregulation of the endothelium following *Staphylococcus aureus* infection, Biochem Soc Trans, 43, 2015, 715-719. Jan. 1, 2015.
Schwegmann, Anita, et al., Host-Directed Drug Targeting of Factors Hijacketed by Pathogens, Sci Signal, uly 22, 2008, 1 (29), 1-8. Jul. 22, 2008.
Loffler, Bettina, et al., *Staphylococcus aureus* persistence in nonprofessional phagocytes, International Journal of Medical Microbiology, vol. 304, No. 2, Mar. 2014, 170-176. Mar. 1, 2014.
Boquet et al., Trends in Cell Biology, 13(5), 2003.
L. Cullen and S. McClean, Bacterial adaptation during chronic respiratory infections, Pathogens. 4 (2015) 66-89.
L. Hong et al., Characterization of a Cdc42 protein inhibitor and its use as a molecular probe, J. Biol. Chem. 288 (2013) 8531-8543.

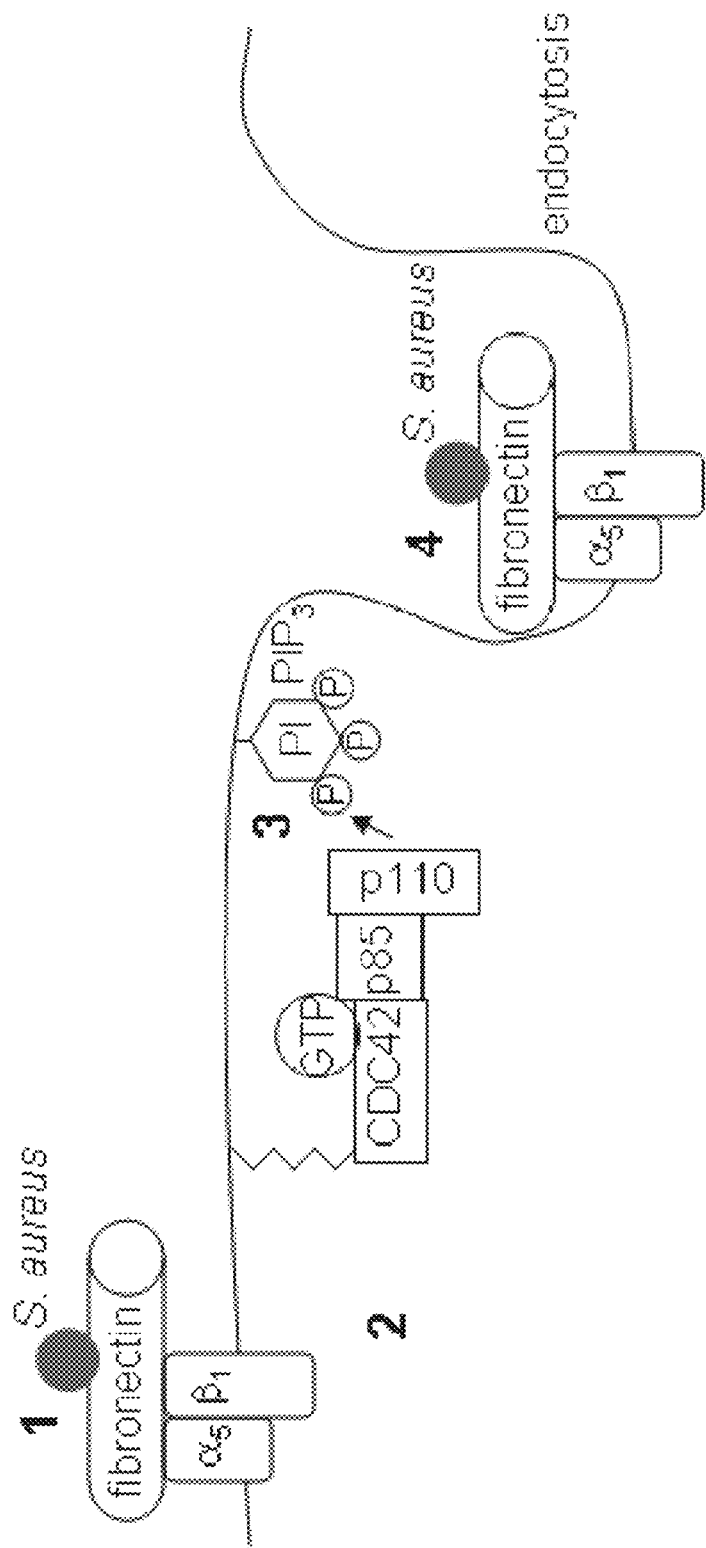

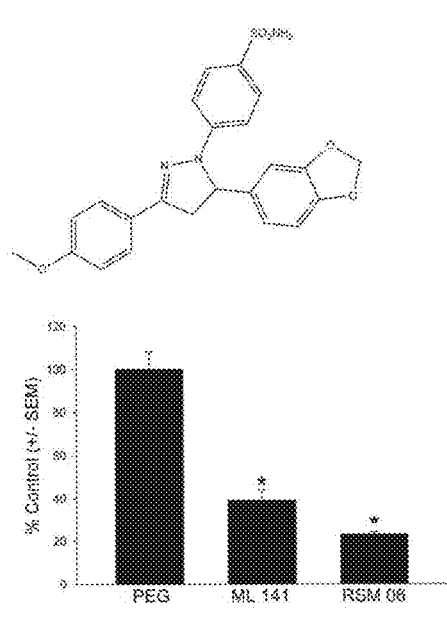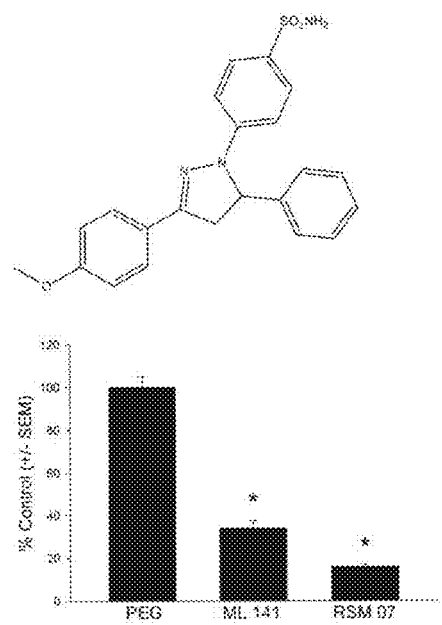
Figure 14C                    Figure 14D

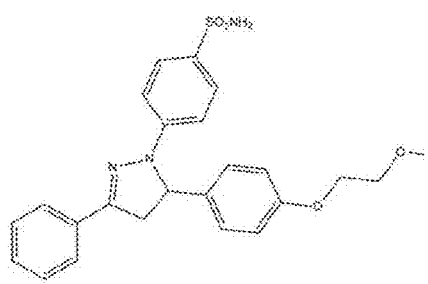
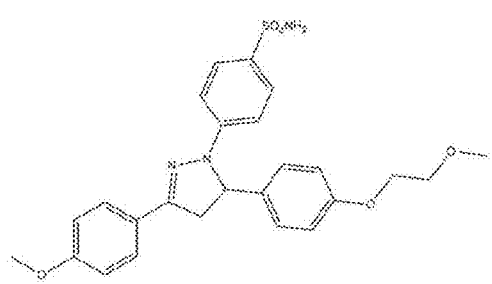
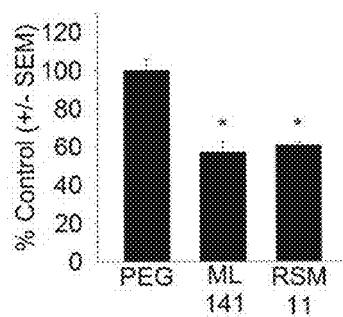
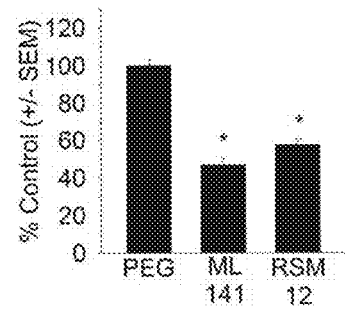
Figure 14E
Figure 14F

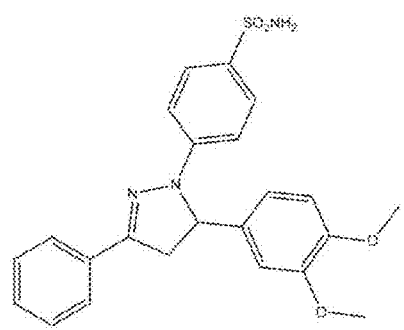
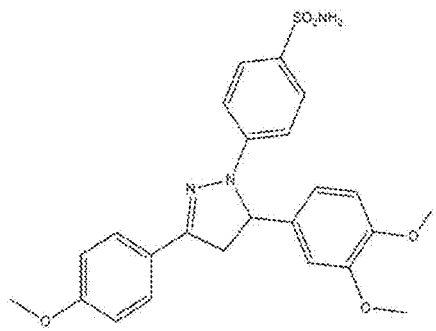
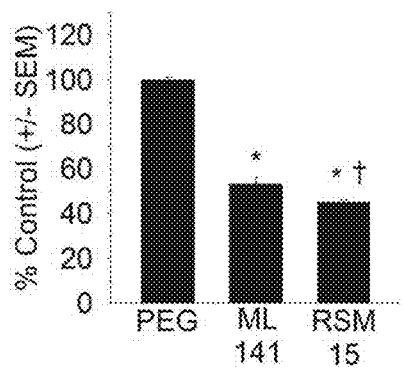
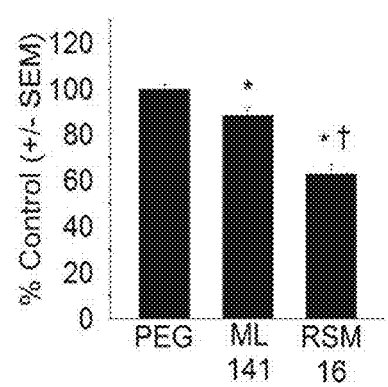
Figure 14I
Figure 14J

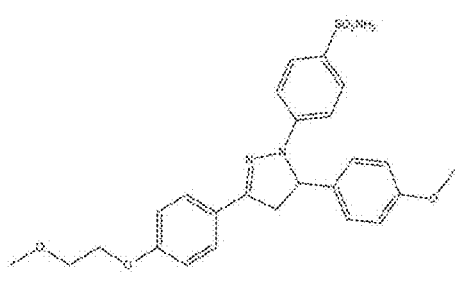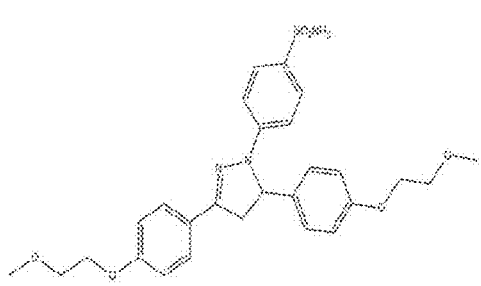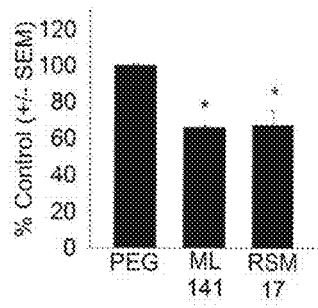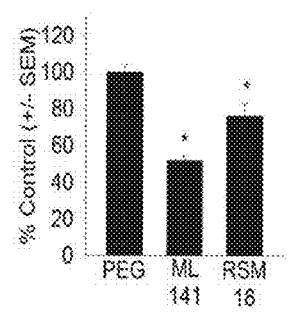
Figure 14K
Figure 14L

RSM 27

RSM 28

RSM 29

RSM 30

RSM 33

METHODS FOR TREATING BACTERIAL INFECTION

CROSS REFERENCE TO RELATED APPLICATION

The present invention claims the benefit of priority as a continuation-in-part to U.S. Non-Provisional patent application Ser. No. 14/561,787, filed Dec. 5, 2014, which claims the benefit of priority to U.S. Provisional Patent Application Ser. No. 61/912,723, filed Dec. 6, 2013, and to U.S. Non-Provisional patent application Ser. No. 13/773,871, filed Feb. 22, 2013, which claims the benefit of priority to U.S. Provisional Patent Application Ser. No. 61/671,054, filed Jul. 12, 2012, Provisional Patent Application Ser. No. 61/644,798, filed May 9, 2012, and U.S. Provisional Patent Application Ser. No. 61/601,807, filed Feb. 22, 2012; all of which are incorporated herein by reference.

GOVERNMENT LICENSE RIGHTS

This invention was made with government support under Grant No. 1 R15 HL092504-01 awarded by the National Institutes of Health, National Heart, Lung and Blood Institute. The U.S. Government has certain rights in the invention disclosed herein.

FIELD

The present disclosure relates to molecules that function as selective modulators (i.e., inhibitors and agonists) of the Ras-homologous (Rho) family of small GTPases and, in particular, CDC42 GTPase, and their use to treat bacterial infection including systemic infection from sources such as *Staphylococcus aureus* and *Streptococcus pyogenes*.

BACKGROUND

In the US, *S. aureus* is the most common etiologic agent in systemic infection and in biofilm-mediated infection of implanted devices. Treatment is complicated by the steady emergence of antibiotic resistance and by increases in elderly, immunocompromised populations, prevalence in the use of surgically implanted devices, and by the ability of both resistant and susceptible strains to persist asymptomatically months to years after the withdrawal of antimicrobial therapy. Severe infection is associated with high rates of mortality (11%-43%) and with chronic, debilitating morbidities that include infective endocarditis, osteomyelitis, and recurrent lung infection. The current cost-of-care is estimated at $10 billion annually for treatment of infection by methicillin resistant *S. aureus* (MRSA) alone.

*S. pyogenes* is the cause of many human diseases, ranging from mild skin infections to life-threatening systemic diseases. An estimated 700 million infections occur worldwide each year, and over 650,000 cases of severe, invasive infections that have a mortality rate of approximately 25%.

Strategies for improving treatment options for *S. aureus* and *S. pyogenes* have included the creation of new antibiotics and the development of adjunctive therapeutics.

SUMMARY

Compounds have been examined that inhibit host cell invasion through a mevalonate independent mechanism. It was found that ML 141 inhibits endothelial cell invasion and intracellular persistence (see FIGS. 1, 2A and 2B). The mode-of-action of ML 141 is distinct from that of other therapeutics used in treating invasions, such as some statins. ML 141 inhibits GTP-binding at the activation site of CDC42. Some statins compete for substrate binding within the catalytic site of 3-hydroxy-3-methylglutaryl (HMG)-CoA reductase. Similar to ML 141, some statins functionally inactivate CDC42 through an indirect mechanism. ML 141 binds directly to CDC42 with a high degree of specificity for this small-GTPase. The mechanism of inhibition by ML 141 also includes decreasing host cell adhesion to fibronectin, the extracellular matrix protein used by *S. aureus* for gaining host cell entry. Inhibition by some statins is not specific for CDC42, but rather is due to diminished levels of isoprenoid intermediates formed from mevalonate within the cholesterol biosynthesis pathway. The isoprenoid intermediates farnesyl pyrophosphate and geranylgeranyl pyrophosphate provide membrane anchoring and protein-protein interactions for CaaX-motif containing proteins that include CDC42. In this way, ML 141 and some statins functionally inhibit CDC42 through different mechanisms.

Host CDC42 may provide a central target in the treatment of invasive infection. CDC42 is used by *S. aureus* to facilitate uptake into host cells and is targeted by staphylococcal toxins for tunneling through endothelial cells to the underlying matrix. This selective use of CDC42 is consistent with invasion by *Streptococcus pneumonia*, the etiologic agent of community-acquired pneumonia, in that redundancy amongst small-GTPases fails to restore invasiveness in cells expressing dominant-negative CDC42. The use of CDC42 to gain host cell entry extends beyond bacterial pathogens to viral infection, facilitating both uptake and replication.

Until recently, the biological relevance of invasiveness by *S. aureus* had been challenged. *S. aureus* had been considered an extracellular pathogen, and intracellular residency appeared to be an in vitro artifact. However, in vivo and clinical evidence supports the concept that intracellular residency by *S. aureus* contributes significantly to pathogenesis by stimulating pro-inflammatory and pro-coagulant responses, by enabling evasion of antibiotics and immune cells, and by establishing intracellular bacterial reservoirs as sources of chronic infection. Numerous questions exist regarding the biological consequence of host cell invasion by *S. aureus*, including whether uptake by non-immune cells serves solely as a mechanism of evasion, or whether this uptake serves as a mechanism of host defense. Studies using ML 141 investigate whether the direct inhibition of CDC42 impedes the roles of this protein in innate immunity.

ML 141 remains largely uncharacterized with respect to antibacterial activity. Synthesis initially was described within a series of compounds predicted to possess antibacterial activity. However, antimicrobial data were not presented. Research found that the compound inhibits GTP-loading of CDC42 with a high degree of specificity for this small-GTPase.

Embodiments disclosed herein provide a method of suppressing microbial infection comprising administering ML 141 or its analogs to cells, where such analogs include the following structure:

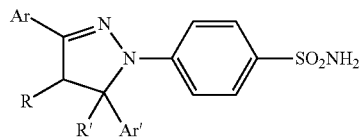

Where Ar' is methoxyphenyl (-Ph-O-Me), R' is hydrogen, and R and Ar are phenylmethylene (-Ph-(2-CH$_2$)—), wherein the phenyl is attached to the Ar position and the methylene is attached to the R position; or Ar' is methoxyphenyl (-Ph-O-Me), R' is methyl, R is hydrogen, and Ar is phenyl; or Ar' is halophenyl (-Ph-halogen), R' is hydrogen, R is hydrogen, and Ar is phenylpolyethylene glycol methyl ether (-Ph-(O—CH$_2$—CH$_2$)$_n$—O-Me) wherein n is any integer.

In some embodiments, the microbial infection is from *Staphylococcus aureus* and/or *Streptococcus pyogenes* and/or an intracellular pathogen that uses fibronectin binding to gain entry into a host cell. In further embodiments, the administering step includes providing ML 141 or its analogs adjacent to the cells. In certain embodiments, the administering step includes testing ML 141 on the cells. In some embodiments, the administering step includes testing at least one analog on the cells. In further embodiments, suppressing microbial infection includes suppressing initial microbial infection. In certain embodiments, suppressing microbial infection includes suppressing persistent microbial infection. In some embodiments, the administering step includes providing approximately 1 µM of ML 141 or its analogs. In even further embodiments, the administering step includes providing approximately 10 µM of ML 141 or its analogs. In certain embodiments, the administering step occurs subsequent to the onset of microbial infection. In some embodiments, the cells are animal cells, are human cells, are from a human and/or are from an animal. In further embodiments, the cells express CDC42.

Embodiments disclosed herein provide a method of suppressing microbial infection comprising providing a chemical including the following structure:

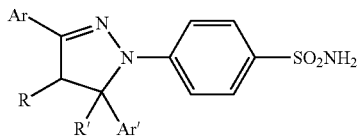

where Ar' is methoxyphenyl (-Ph-O-Me), R' is hydrogen, and R and Ar are phenylmethylene (-Ph-(2-CH$_2$)—), wherein the phenyl is attached to the Ar position and the methylene is attached to the R position; or Ar' is methoxyphenyl (-Ph-O-Me), R' is methyl, R is hydrogen, and Ar is phenyl; or Ar' is halophenyl (-Ph-halogen), R' is hydrogen, R is hydrogen, and Ar is phenylpolyethylene glycol methyl ether (-Ph-(O—CH$_2$—CH$_2$)$_n$—O-Me) wherein n is any integer; and providing the chemical to cells. In some embodiments, the method further comprises providing a pharmaceutically accepted solvent or delivery vehicle selected from the group consisting of polyethylene glycol (PEG), dimethyl sulfoxide, ethanol, and combinations thereof. In certain embodiments, the solvent or delivery vehicle is polyethylene glycol. In other embodiments, the halophenyl is chlorophenyl.

Embodiments disclosed herein provide a method of suppressing microbial infection comprising administering ML 141 or its analogs to cells, where such analogs include the following structures:

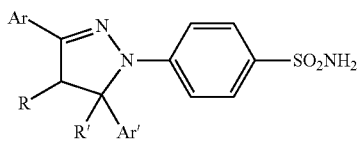

where Ar is phenyl, acetamidophenyl (-Ph-NH—CO-Me), or propanamidophenyl (Ph-NH—CO-Et), R is hydrogen, R' is hydrogen, and Ar' is methoxyphenyl (-Ph-O-Me), acetamidophenyl (-Ph-NH—CO-Me), or dimethylaminophenyl (Ph-N-Me2); and

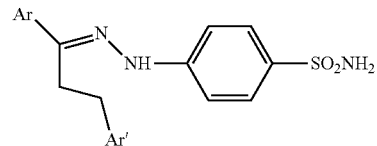

where Ar is phenyl and Ar' is methoxyphenyl (-Ph-O-Me).

BRIEF DESCRIPTION OF THE DRAWINGS

The above-mentioned and other features of this disclosure, and the manner of attaining them, will become more apparent and the disclosure itself will be better understood by reference to the following description of embodiments of the disclosure taken in conjunction with the accompanying drawings, wherein:

FIG. 2A is a schematic model of *Staphylococcus aureus* host cell invasion in the absence of ML 141. Step 1: In the absence of ML 141, *S. aureus* bound to host fibronectin interacts with the host cell integrin $\alpha_5\beta_1$, stimulating GTP-loading and activation of CDC42. Step 2: GTP-loading of CDC42 increases affinity for the p85α regulatory subunit of phosphoinositide 3-kinase (PI3K). CDC42, coupled to PI3K through the p85α subunit, positions the catalytic domain p110α in proximity with phosphoinositide 4,5-bisphosphate (PI$_{4,5}$). Step 3: The product of the phosphorylation of PI$_{4,5}$ by p110α is PI 3,4,5-trisphosphate (PIP$_3$), capable of promoting endocytosis of the bacterium/fibronectin/integrin complex, as illustrated by Step 4.

FIG. 4A-1 illustrates by histogram overlay how ML 141 inhibits host cell invasion. Human umbilical vein endothelial cells (HUVEC) were pretreated (18 hours) with the vehicle control polyethylene glycol (PEG) or ML 141 (10 µM) suspended in PEG. Following infection by Alexa Fluor 488-labeled *Staphylococcus aureus* (1 hour), extracellular bacteria were removed using the antimicrobials gentamicin and lysostaphin. Infected cells (identified by 488 fluorescence) were detected by flow cytometry and represented by histogram overlay.

FIG. 4A-2 illustrates by averaged mean fluorescence intensity values how ML 141 inhibits host cell invasion. Human umbilical vein endothelial cells (HUVEC) were pretreated (18 hours) with the vehicle control polyethylene glycol (PEG) or ML 141 (10 µM) suspended in PEG. Following infection by Alexa Fluor 488-labeled *Staphylococcus aureus* (1 hour), extracellular bacteria were removed using the antimicrobials gentamicin and lysostaphin. Infected cells (identified by 488 fluorescence) were detected by flow cytometry and represented by histogram overlay as illustrated in FIG. 4A-1 and averaged mean fluorescence intensity values (*less than vehicle control; p ≤ 0.001 by Student's t-test; n=3-5/treatment).

FIG. 4B-1 illustrates by histogram overlay how ML 141 inhibits host cell invasion. Human umbilical vein endothelial cells (HUVEC) were pretreated (18 hours) with the vehicle control dimethyl sulfoxide (DMSO) or ML 141 (10 µM) suspended in dimethyl sulfoxide (DMSO). Following infection by Alexa Fluor 488-labeled *Staphylococcus aureus* (1 hour), extracellular bacteria were removed using the antimicrobials gentamicin and lysostaphin. Infected cells (identified by 488 fluorescence) were detected by flow cytometry and represented by histogram overlay.

FIG. 4B-2 illustrates by averaged mean fluorescence intensity values how ML 141 inhibits host cell invasion. Human umbilical vein endothelial cells (HUVEC) were pretreated (18 hours) with the vehicle control dimethyl sulfoxide (DMSO) or ML 141 (10 µM) suspended in dimethyl sulfoxide (DMSO). Following infection by Alexa Fluor 488-labeled *Staphylococcus aureus* (1 hour), extracellular bacteria were removed using the antimicrobials gentamicin and lysostaphin. Infected cells (identified by 488 fluorescence) were detected by flow cytometry and represented by histogram overlay as illustrated in FIG. 4B-1 and averaged mean fluorescence intensity values (*less than vehicle control; p≤0.001 by Student's t-test; n=3-5/treatment).

FIG. 14C is a depiction of the chemical structure of the RSM 06 structural analog of ML 141 and a chart indicating its ability to inhibit *Staphylococcus aureus* invasion of human umbilical vein endothelial cells as compared to ML141 and a PEG control.

FIG. 14D is a depiction of the chemical structure of the RSM 07 structural analog of ML 141 and a chart indicating its ability to inhibit *Staphylococcus aureus* invasion of human umbilical vein endothelial cells as compared to ML141 and a PEG control.

FIG. 14E is a depiction of the chemical structure of the RSM 11 structural analog of ML 141 and a chart indicating its ability to inhibit *Staphylococcus aureus* invasion of human umbilical vein endothelial cells as compared to ML141 and a PEG control.

FIG. 14F is a depiction of the chemical structure of the RSM 12 structural analog of ML 141 and a chart indicating its ability to inhibit *Staphylococcus aureus* invasion of human umbilical vein endothelial cells as compared to ML141 and a PEG control.

FIG. 14I is a depiction of the chemical structure of the RSM 15 structural analog of ML 141 and a chart indicating its ability to inhibit *Staphylococcus aureus* invasion of human umbilical vein endothelial cells as compared to ML141 and a PEG control.

FIG. 14J is a depiction of the chemical structure of the RSM 16 structural analog of ML 141 and a chart indicating its ability to inhibit *Staphylococcus aureus* invasion of human umbilical vein endothelial cells as compared to ML141 and a PEG control.

FIG. 14K is a depiction of the chemical structure of the RSM 17 structural analog of ML 141 and a chart indicating its ability to inhibit *Staphylococcus aureus* invasion of human umbilical vein endothelial cells as compared to ML141 and a PEG control.

FIG. 14L is a depiction of the chemical structure of the RSM 18 structural analog of ML 141 and a chart indicating its ability to inhibit *Staphylococcus aureus* invasion of human umbilical vein endothelial cells as compared to ML141 and a PEG control.

DETAILED DESCRIPTION OF THE EXEMPLARY EMBODIMENTS

The embodiments disclosed below are not intended to be exhaustive or limit the disclosure to the precise forms disclosed in the following detailed description. Rather, the embodiments are chosen and described so that others skilled in the art may utilize their teachings.

Innovation

The ML 141 compound has been used to address whether targeting CDC42 limits persisting intracellular populations, diminishing this source of chronic infection and initiates pleiotropic effects by interrupting the PI3K signaling pathway.

Findings will impact the characterization of this potentially first-in-class molecule for the development of adjunctive therapeutics. Moreover, data from the in vivo toxicity study as well as the synthesis of analogs potentially will be of use to the broader scientific community for exploring the role of CDC42 in a range of disease states.

Approach

Preliminary Data

Figure 1:
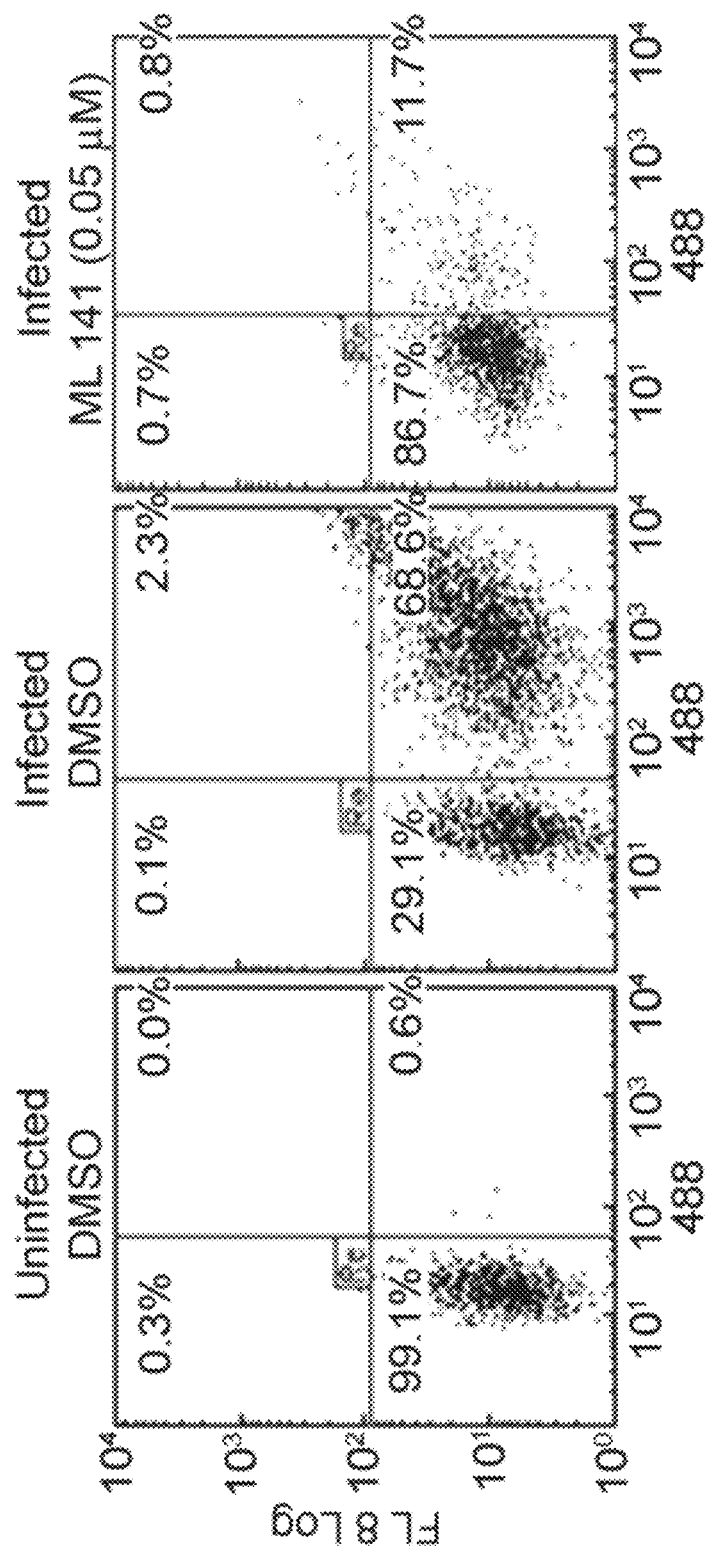
FIG. 1 illustrates ML 141 limits host cell invasion. The monocytic cell line U937 was pretreated with the vehicle control dimethyl sulfoxide (DMSO) or with ML 141 (0.05 µM, 1 h) followed by infection with Alexa Fluor 488-labeled *S. aureus* (1 hour). The % of 488$^+$ cells decreased with ML 141 treatment.
Figure 2B:
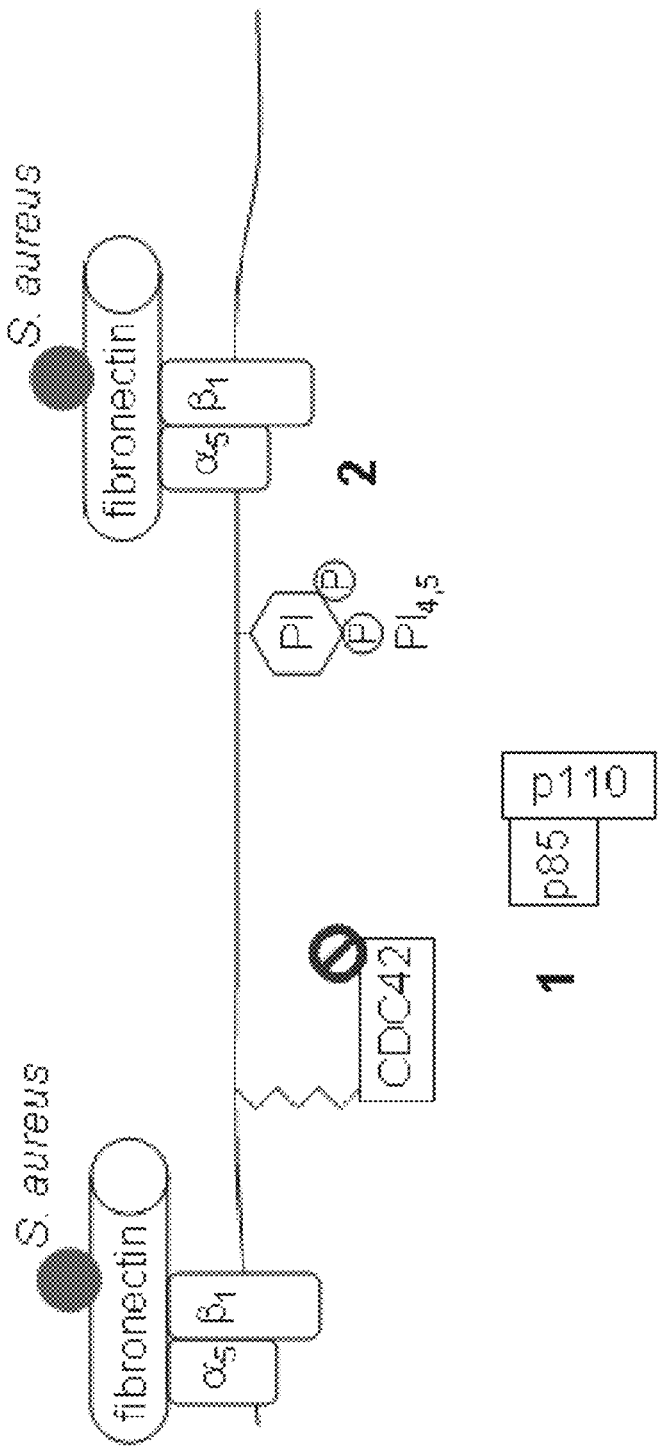
FIG. 2B is a schematic model of *Staphylococcus aureus* host cell inhibition by ML 141. Step 1: In response to the inhibition of GTP-loading of CDC42 by ML 141, CDC42 remains uncoupled from p85α. Consequently, p110α remains within the cytosol. By sequestering p110α within the cytosol, membrane-bound PI$_{4,5}$ is not accessible, diminishing PIP$_3$ production. Step 2: In the absence of PIP$_3$, endocytic uptake of the bacterium/fibronectin/integrin complex is limited, protecting the host cell from bacterial invasion (models are based on references indicated in text and on current study).

Direct Inhibition of CDC42 Diminishes Host Cell Invasion:

Specific pharmacologic inhibition of CDC42 has been examined to determine whether it is sufficient in the inhibition of host cell invasion by S. aureus. It was found that pretreatment (0.05 µM, 1 hour) decreased invasion by S. aureus as shown in FIG. 1. Host cell cytotoxicity was undetectable below 30 µM in vitro. The highest concentration of ML 141 introduced in vivo without detectable toxicity was 100 mg/kg body weight [BW]. The compound was dissolved in polyethylene glycol and administered as a single intraperitoneal injection to C57BL/6 mice.

Figure 3:
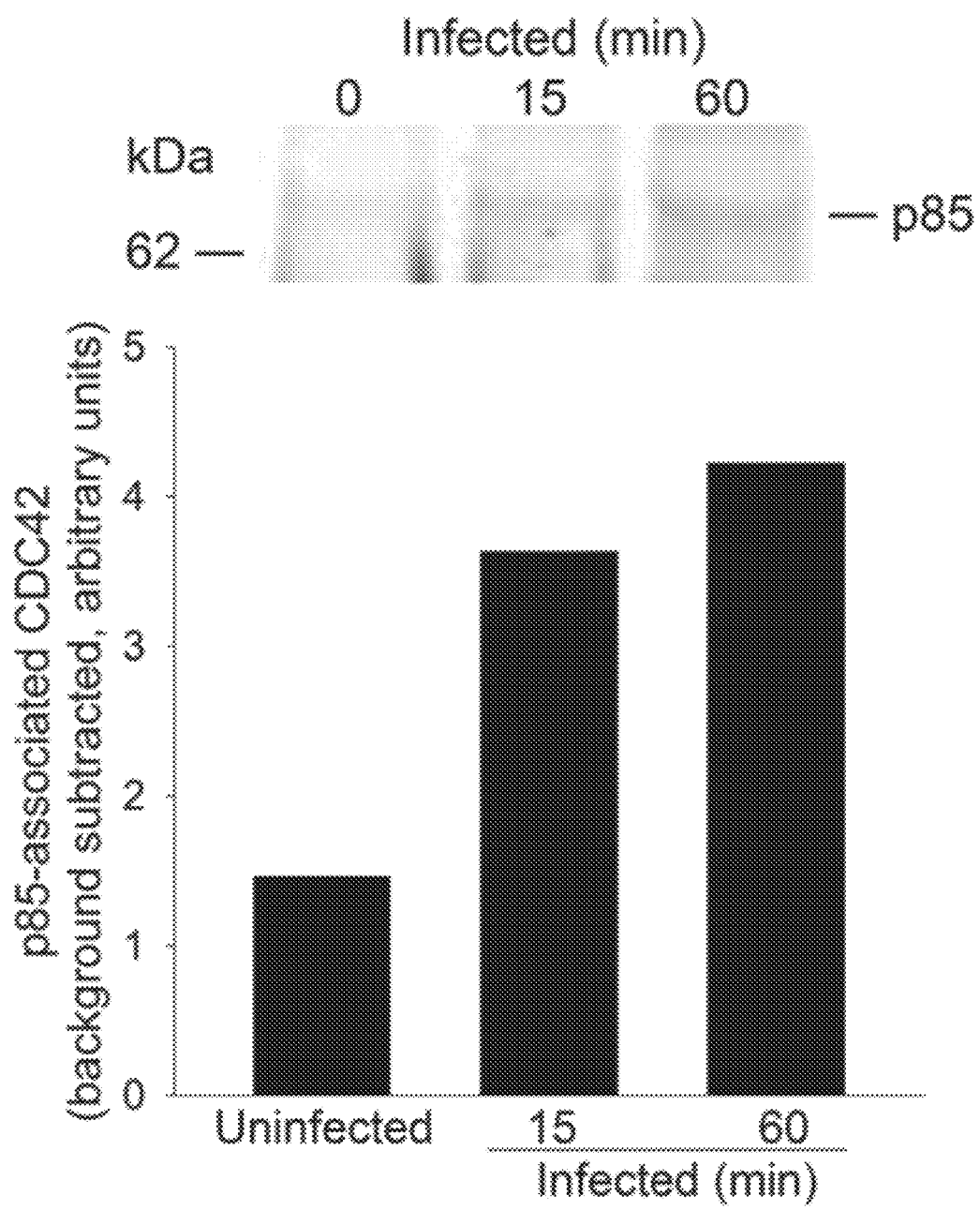
FIG. 3 illustrates how invasion stimulates coupling between CDC42 and the downstream effector phosphoinositide 3-kinase (PI3K) p85. Host cells (human embryonic kidney cells) were infected for 15 or 60 min, lysates immunoprecipitated (IP) with anti-CDC42, and immunoblot (IB) probed with anti-p85 followed by Alexa Fluor anti-rabbit 800CW. Fluorescence was detected using the Odyssey Infrared Imaging System. Integrated intensities and background correction were performed using Odyssey software.

ML 141 Diminishes Intracellular Persistence:

Host Invasion Stimulates Coupling Between CDC42 and PI3Kp85α:

Affinity between the downstream regulator PI3Kp85α and CDC42 is enhanced by GTP-loading of CDC42. Earlier research has demonstrated that S. aureus host cell invasion stimulates GTP-loading of CDC42, raising the possibility that invasion potentially results in increased coupling between these proteins. Within 15 min of host cell invasion, it was found that p85α-associated CDC42 had increased (see FIG. 3).

Summary of Preliminary Data

Preliminary research indicates that ML 141 inhibits invasiveness and intracellular persistence potentially through impaired PI3K signaling. The following Experimental Sections examine ML 141 to investigate the targeting of CDC42 in ameliorating clinically relevant, persistent infection by S. aureus.

Experimental Section 1: Examine ML 141 in Limiting Persisting S. aureus Infection Rationale Increasing evidence supports the hypothesis that S. aureus infection persists through pathogenic mechanisms that includes survival within host cells. The focus of Section 1 is on exploring new strategies for limiting infection by this mechanism. It was found that ML 141 decreased initial host cell invasion and the number of persistently infecting, intracellular bacteria (see FIGS. 1 and 2). A subset of bacteria that persist intracellularly can convert phenotypically to what have been termed "small colony variants" (SCV). This phenotypically distinct population has been the source of controversy, questioned as a laboratory artifact. However, recent in vivo and clinical evidence supports the existence of this population and its potential contribution to chronic, recurrent infection. These variants, upon release from persistently infected host cells, invade new host cells more aggressively than their parental strain. It is believed that ML 141 limits this potential source of recurrent infection by inhibiting their uptake into new host cells, increasing their clearance by antibiotic therapy and exposure to surveillance by immune cells. Alternatively, ML 141 would impair uptake of S. aureus by non-immune cells as a mechanism of clearance.

Study 2

Materials and Methods

Reagents for Cultured Cells:

The following were used at the concentrations and durations indicated within each figure or method described below: paraformaldehyde (Electron Microscopy Sciences, Hatfield, Pa.); dimethyl sulfoxide (DMSO) and bovine serum albumin (BSA, Thermo Fisher Scientific, Pittsburgh, Pa.); tryptic soy agar (TSA) and broth (TSB), saponin, lysostaphin, gentamicin, triton, polyethylene glycol (PEG), and formaldehyde (Sigma-Aldrich, St. Louis, Mo.); phosphate buffered saline (PBS), Attachment Factor, M200, Low Serum Growth Supplement (LSGS), rabbit anti-mouse IgG, Alexa Fluor 488 phalloidin, and L-glutamine (Life Technologies, Carlsbad, Calif.); XTT (Biotium, Hayward, Calif.); and fetal bovine serum (FBS, Atlanta Biologicals, Lawrenceville, Ga.). 4-[3-(4-methoxyphenyl)-5-phenyl-3,4-dihydropyrazol-2-yl]benzenesulfonamide (ML 141) was generously provided by Dr. Jennifer Golden of the University of Kansas Specialized Chemistry Center or was prepared following standard synthetic procedures.

Cell Culture and Compound Treatment:

In one embodiment, human umbilical vein endothelial cells (HUVEC, Life Technologies) are cultured in M200 medium supplemented with LSGS. RAW 264.7 cells (American Type Culture Collection, ATCC, Manassas, Va.) are cultured in RPMI supplemented with 10% FBS and L-glutamine. All cell types are maintained at 5% $CO_2$, 37° C., in 75 $cm^2$ vented cap flasks (Thermo-Fisher). For assays, cultured cells are plated at $1\times10^5$ cells/ml in 35 mm culture dishes coated with Attachment Factor. The next day, cells are pretreated in culture medium containing the vehicle control or ML 141. For compound delivery, ML 141 first is suspended into DMSO or into PEG at a concentration of 5 mM. The 5 mM solution is diluted to 1 mM in the solvent and then diluted to the final concentration for each experiment in either serum-containing or serum-free medium. For vehicle control treatment, the same volume of PEG or DMSO as that of ML 141 is added to medium. The following day, the invasion assay is performed. For the shorter duration experiments, compound is added on the same day as the invasion assay, 1 hour prior to bacteria. Because in vitro data indicate that ML 141 is a reversible inhibitor, bacteria are added directly to medium containing vehicle control or ML 141.

In another embodiment, HUVEC (Millipore, Billerica, Mass.) are cultured in EndoGRO LS Complete Media (Millipore) and are maintained at 5% $CO_2$, 37° C., in 75 $cm^2$ vented cap flasks (Thermo-Fisher). For the invasion assay, cultured cells are plated at $1\times10^4$ cells/ml in 96-well culture dishes coated with Attachment Factor. The next day, cells are pretreated in culture medium containing the vehicle control, ML 141, or ML 141 structural analog. For compound delivery, ML 141 and structural analogs first are suspended into PEG at a concentration of 5 mM. The 5 mM solution is diluted to 1 mM in the solvent and then is diluted to the final concentration for each experiment in serum containing medium. For vehicle control treatment, the same volume of PEG as that of ML 141 or of ML 141 structural analog is added to the medium. The following day, the invasion assay is performed. Bacteria are added directly to medium containing vehicle control, ML 141, or the ML 141 structural analog.

Invasion Assay:

Two days prior to the assay, TSB is inoculated with *S. aureus* (American Type Culture Collection #29213) and incubated overnight (225 rpm, 37° C.). Bacteria are subcultured the next day into fresh TSB. On the day of the assay, bacteria are pelleted (10000×g, 37° C., 3 min), are washed in saline, are pelleted as above, are resuspended in saline, then fluorescently labeled by incubation with rabbit anti-mouse IgG Alexa Fluor 488 (final concentration 8 µg/ml, RT, 20 min). Protein A, a *S. aureus* cell surface protein, avidly binds IgG thereby labeling the bacteria. Labeled bacteria are washed twice as above and are resuspended to $3\times10^8$ CFU/ml in saline. Host cells are incubated with the bacteria for 1 hour ($1.2\times10^8$ CFU/ml for same-day recovery, $5\times10^6$ for recovery after 48 hours, $1.4\times10^7$ CFU/ml; 5% $CO_2$, 37° C.). Following infection, extracellular bacteria are removed by extensive washes with PBS and incubation of the host cells with antimicrobials that have limited mammalian membrane permeability (lysostaphin, 20 µg/ml and gentamicin, 50 µg/ml; 45 min for same-day recovery studies, 48 hours for 2-day recovery studies; 5% $CO_2$, 37° C.). To detect the level of infection using flow cytometry, cells that have been infected with fluorescently-labeled bacteria are washed extensively with PBS, lifted from 96-well plate by incubation with trypsin, washed extensively in FACS buffer (2% BSA/0.1% sodium azide/PBS), fixed (FACS buffer containing 0.74% formaldehyde), and are counted using an Accuri flow cytometer (BD, Franklin Lakes, N.J.). They are also lifted from culture dishes using cell scrapers, pelleted, fixed (1% BSA/0.74% formaldehyde/PBS), and are counted using an Accuri flow cytometer. For enumeration of the infecting bacteria, intracellular bacteria are released from host cells using 1% saponin/PBS (20 min, 5% $CO_2$, 37° C.) and serial dilutions are plated on TSA (16 hours, 37° C.). For infection under serum free conditions, bacteria first are incubated in FBS (15 minutes, RT) followed by extensive washing. The serum incubation provided extracellular matrix proteins that facilitate invasive infection.

Cytotoxicity Assay:

HUVEC are plated at a density of $1.2\times10^4$ cells/ml into 96-well dishes coated with Attachment Factor. The next day, cells are pretreated with the vehicle control DMSO or with ML 141 (18 hours). An XTT-reducing assay is performed and absorbance read at 490 nanometers using a Bio-Rad plate reader.

Assessment of Bactericidal Activity:

HUVEC are pretreated with the vehicle control DMSO or with ML 141 (18 hours) then incubated with $5\times10^6$ CFU/ml (1 hour). Following infection, the medium from each plate is removed, is serially diluted into saline, and is plated on fresh blood agar plates. The next day, colony counts are performed and hemolysis is recorded.

Immunofluorescence:

HUVEC are plated at $1\times10^5$ cells/ml into 35 mm glass-bottom dishes (MatTek, Ashland, Mass.) are coated with Attachment Factor, are pretreated, and are infected ($1.2\times10^8$ CFU) as described above. Following infection, cells are washed with 1×PBS, fixed (4% paraformaldehyde/PBS, 30 min), permeabilized, blocked (0.1% Triton, 1% bovine serum albumin, 30 min), and incubated with Alexa Fluor 488 phalloidin (1:40). Confocal images are acquired using an inverted Zeiss Axiovert200 microscope equipped with a plan-apochromat 40×, 1.2 NA water immersion lens with correction collar and LSM 5 Pascal scan head. Alexa 488 is excited by the 488 nanommeter Ar laser line and is detected using a 505-530 nanometer bandpass filter. Z-sectioning and frame size are set to Nyquist sampling. Maximum pixel projections from the Z-stacks are generated and are analyzed for actin morphology.

Statistical Analyses:

Normally distributed data are analyzed by Student's t-test when the comparison was limited to 2 groups or by one-way ANOVA followed by Student-Newman-Keuls post-hoc analysis when 3 or more groups were compared (Sigma Stat, Systat, Point Richmond, Calif.). Differences between groups were considered statistically significant at $p<0.05$.

Results and Discussion

ML 141 Limits Host Cell Invasion.

Figures 1, 4A:
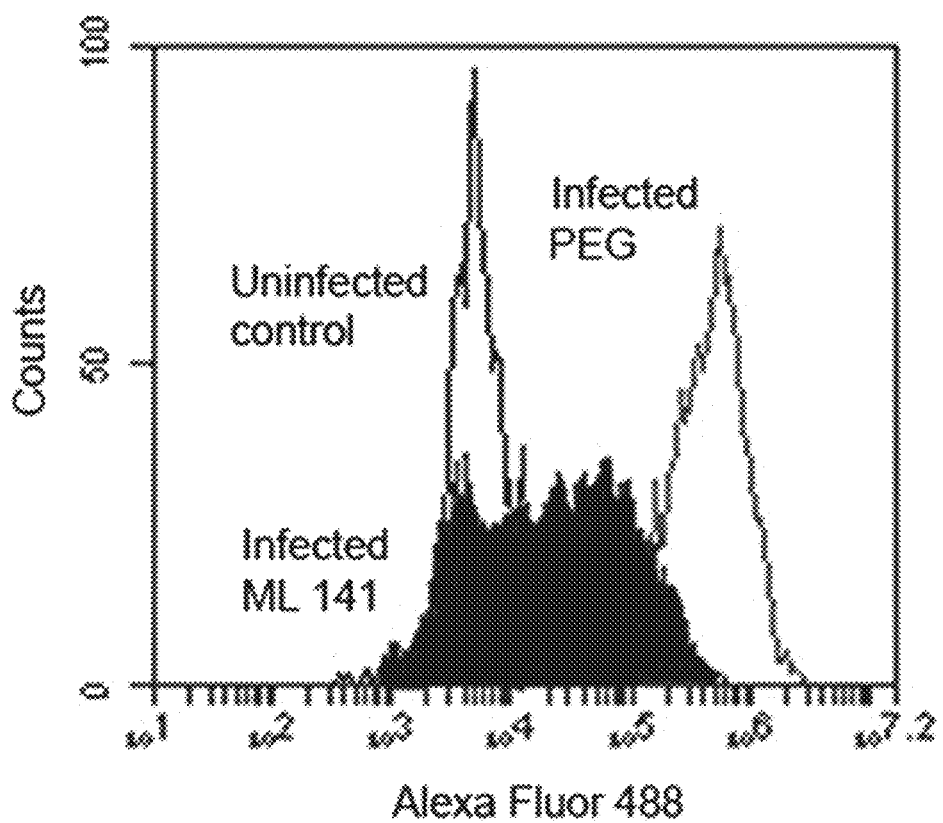
Figures 2, 4A:
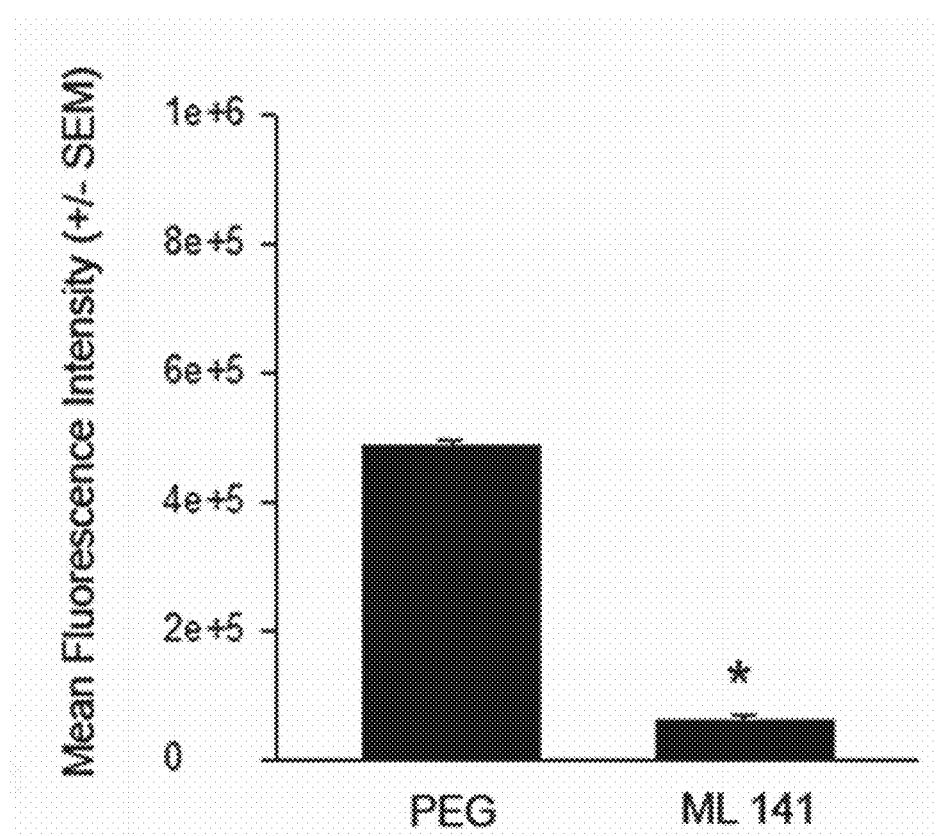
Figures 1, 4B:
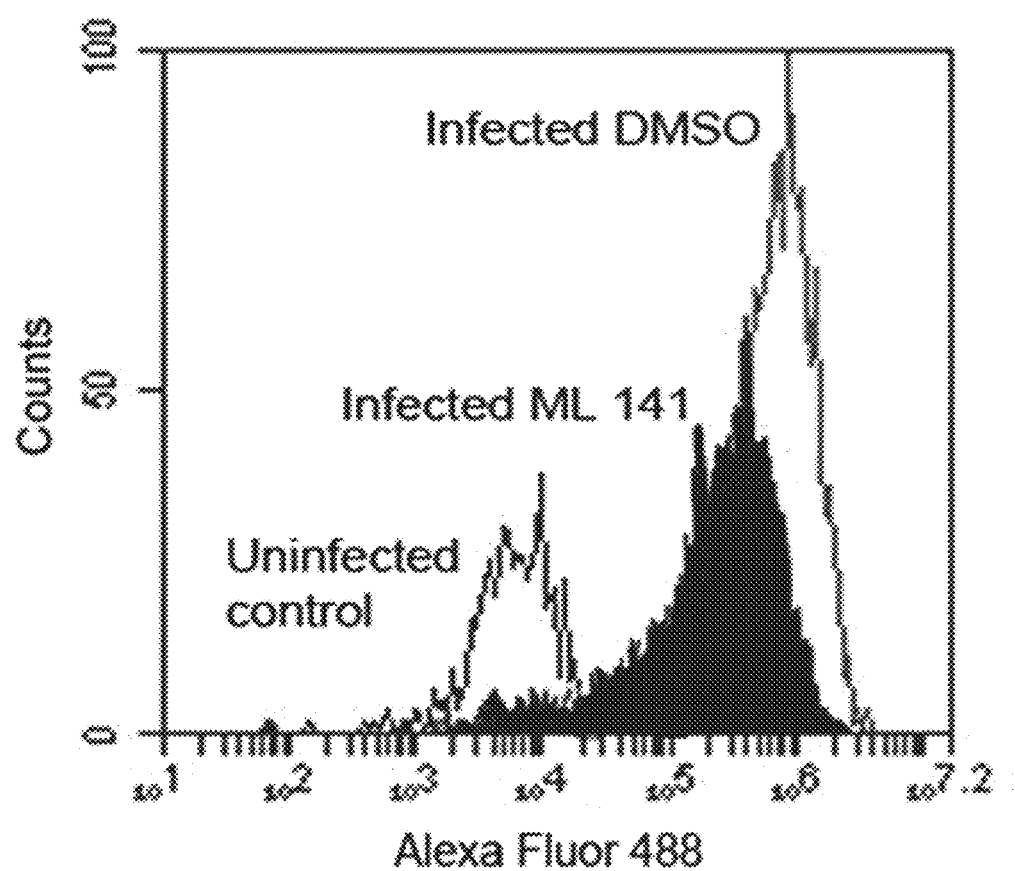
Figures 2, 4B:
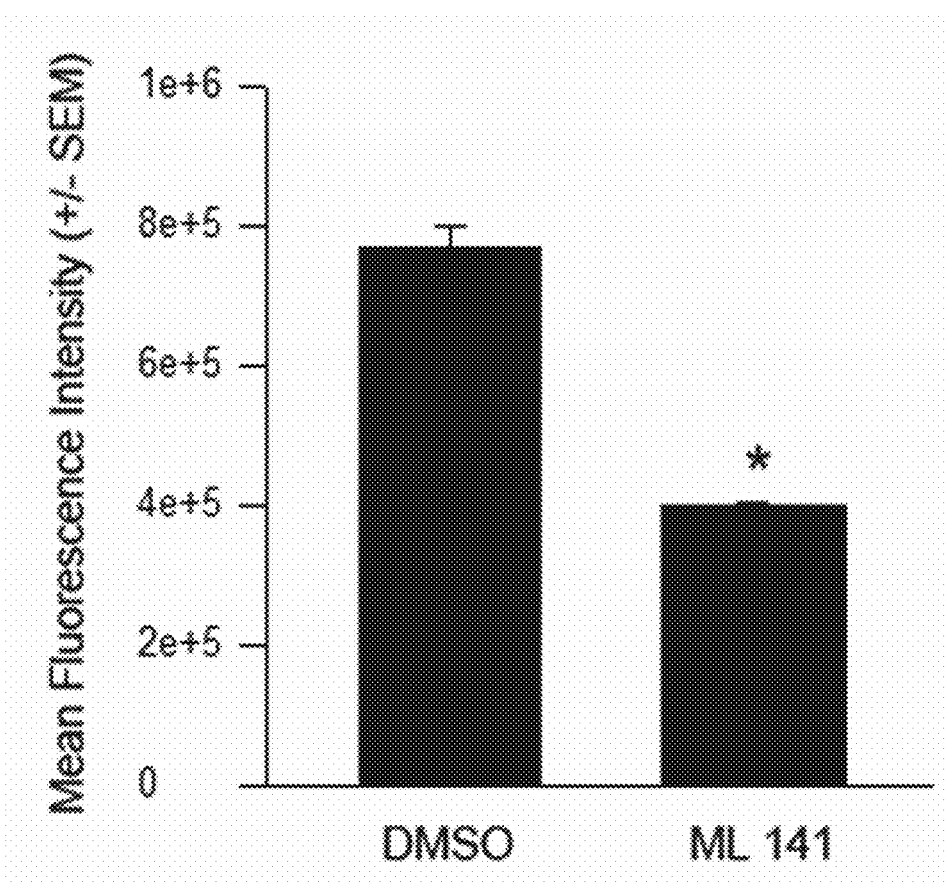
Figure 5:
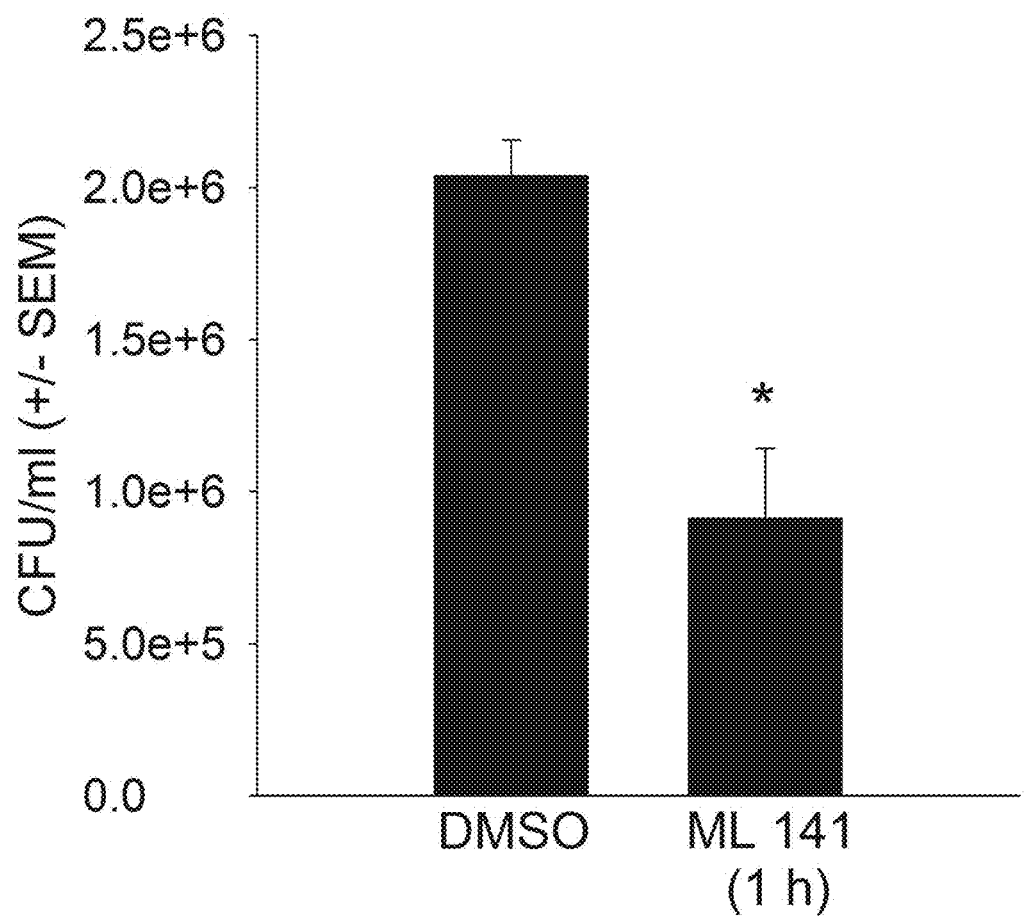
FIG. 5 is a graph illustrating ML 141 inhibiting invasion with shorter duration exposure under serum starved conditions. RAW 264.7 cells were serum-starved overnight then pretreated for 1 hour with the vehicle control dimethyl sulfoxide (DMSO) or with ML 141 (10 µM). Following infection with *Staphylococcus aureus* (1 hour), extracellular bacteria were eliminated using the antimicrobials gentamicin and lysostaphin (45 minutes), and intracellular bacteria recovered by permeabilizing the host cells. Serial dilutions of the recovered intracellular bacteria were incubated on tryptic soy agar, colonies enumerated, and colony forming units (CFU)/ml calculated (*less than vehicle control; p≤0.05 by Student's t-test; n=3/treatment).

Earlier work had indicated that CDC42 activity is stimulated by *S. aureus* host cell invasion and that limiting CDC42 function using a genetic strategy led to a reduction in *S. aureus* invasiveness. To determine whether specific, pharmacologic inhibition of CDC42 is sufficient to inhibit invasion by *S. aureus*, HUVEC are pretreated (18 hours) with ML 141 (10.0 µM) or with the vehicle control PEG and are infected for 1 hour. ML 141 treatment decreased invasion by more than 80% ($p\le0.001$ by Student's t-test, FIG. 4, Panel A). When ML 141 is delivered in DMSO rather than in PEG, inhibition nears 50% (Panel B). Inhibition is detectable when treatment was reduced from 18 hours to 1 hour under serum-starved conditions (FIG. 5). ML 141 inhibited invasion in all cell types examined (HUVEC, HEK, U-87 MG, RAW and A549).

Figure 6A:
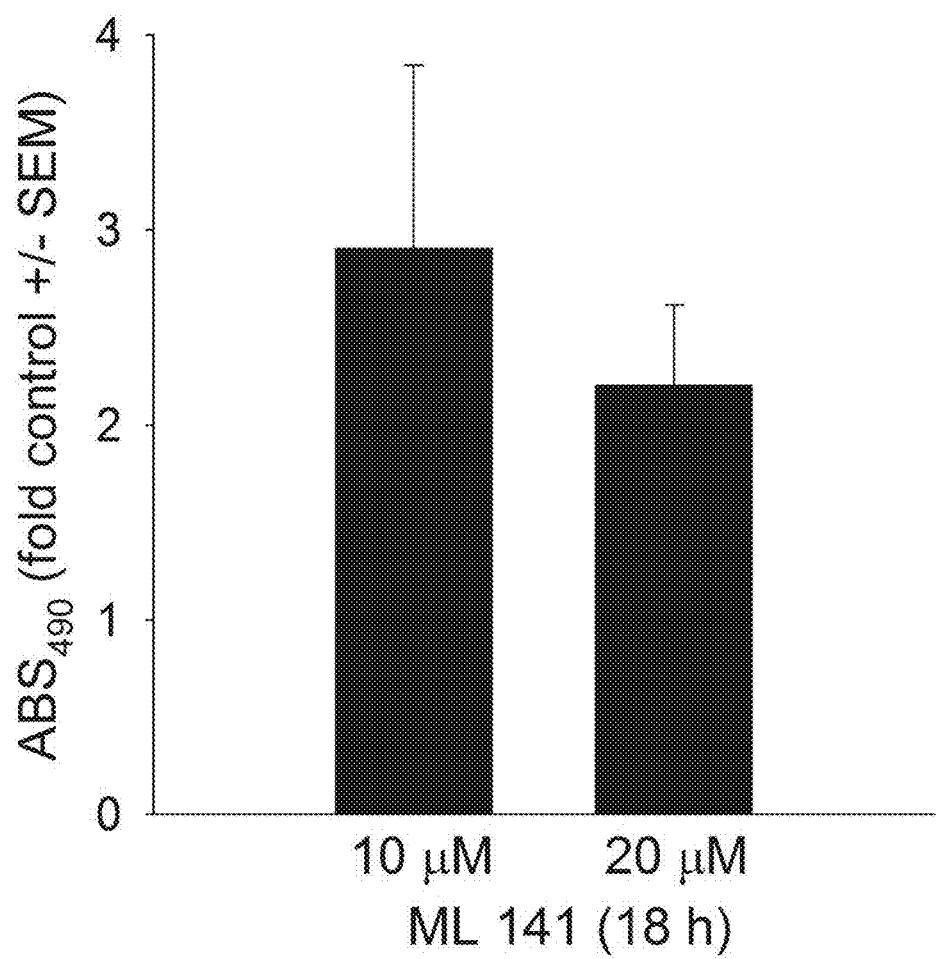
FIG. 6A illustrates that neither cytotoxicity nor bactericidal activity is detected. Human umbilical vein endothelial cells (HUVEC) were pretreated (18 hours) with the vehicle control polyethylene glycol (PEG) or with ML 141 and viability assessed using an XTT assay. The formazan dye produced in living cells was detectable at an absorbance wavelength of 490 nanometers and used as an indicator of cell viability. Absorbance values were not different amongst the groups (p>0.05 by one-way ANOVA; n=3/treatment).
Figure 6B:
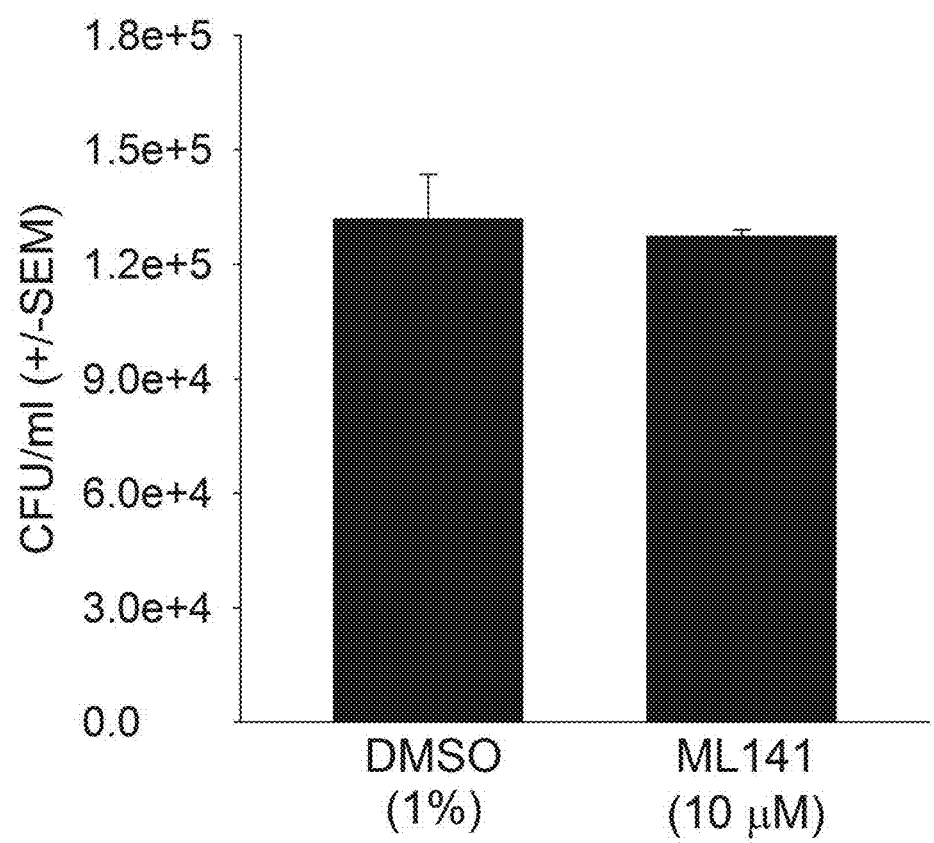
FIG. 6B illustrates that neither cytotoxicity nor bactericidal activity is detected. Cultures of *Staphylococcus aureus* that had been incubated with the vehicle control DMSO or with ML 141 (1 hour, 37° C., 225 rpm) were serially diluted, plated onto blood agar, and incubated (18 hours, 37° C.). Colonies were enumerated and colony forming units (CFU)/ml determined. CFU/ml were not different amongst the groups (p>0.05 by t-test; n=2/treatment).

The number of uninfected cells is greatest when ML 141 has been delivered in PEG rather than in DMSO (FIGS. 4A-1-4B-2), suggesting that PEG enhanced the delivery of ML 141. PEG is a well-characterized, hydrophilic polymer that can increase the delivery of hydrophobic compounds into mammalian cells. The increased effectiveness of ML 141 when delivered in PEG may be attributable to an increase in the solubility of ML 141. Evidence supporting this concept is that suspension in PEG enhances the solubility of celecoxib, a COX-2 inhibitor that is structurally similar to ML 141. That PEG generally is well-tolerated with minimal toxicity is supported by the finding that cytotoxicity was not observed at the concentrations used in the invasion assay (FIGS. 6A-6B).

Cytotoxicity and Bactericidal Activity were not Detected.

To determine whether host or bacterial cell death contributed to the decreases in recovered bacteria, cytotoxicity and bactericidal activity are assessed. Cytotoxicity is not detectable in HUVEC treated overnight in ML 141 in the PEG solvent (FIG. 6A; $p\ge0.05$ by one-way ANOVA). Bactericidal activity was not detected (FIG. 6B). These findings suggest that the decreases in infected host cells and in recovered bacteria are attributable to diminished host cell invasion rather than to host cell death or to bactericidal activity of the compound.

Intracellular Populations Remain Suppressed Over Time.

Figure 7:
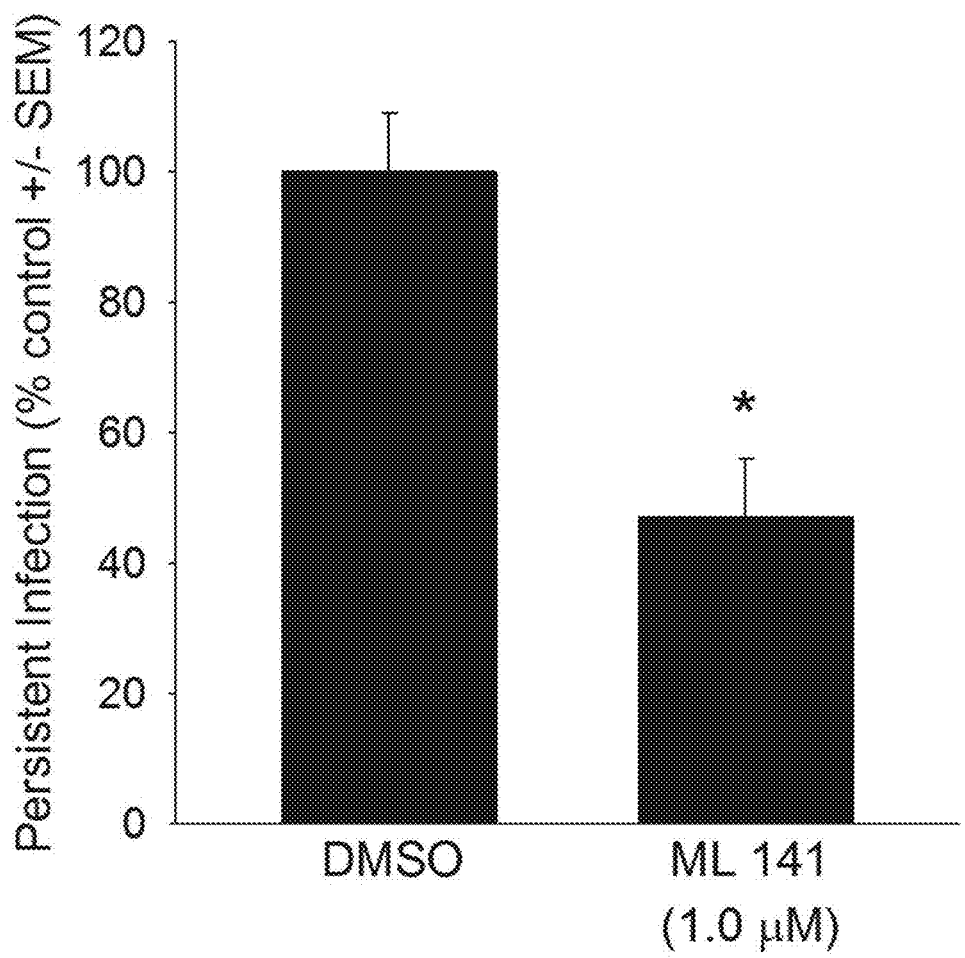
FIG. 7 is a graph illustrating suppression of intracellular population sustained over time. Human umbilical vein endothelial cells (HUVEC) were pretreated (1.0 µM, 18 hours) with the vehicle control dimethyl sulfoxide (DMSO) or ML 141 and infected with *Staphylococcus aureus* (1 hour). At 48 hours, intracellular bacteria were recovered, serial dilutions incubated on tryptic soy agar and colonies enumerated. Data are presented as % control, ±SEM (*less than vehicle control; p≤0.05 by t-test; n=3-5/treatment).

Intracellular bacterial populations can continue to proliferate, therefore, the intracellular bacterial population within ML 141-treated host cells was examined to determine whether it returned to control levels over time. HUVEC are pretreated with vehicle control or with ML 141 (1.0 µM, 18 hours), infected for 1 hour, and bacterial levels within host cells are assessed at 48 hours post infection. These experiments are pursued in endothelial cells as a model system for growth of intracellular reservoirs and because of the central role played by the endothelial cell in the pathogenesis of endocarditis. Treatment with ML 141 diminished the number of viable bacteria recovered 48 hours post-infection (FIG. 7).

Intracellular persistence by *S. aureus* enables the pathogen to evade antibiotic therapies and surveillance by immune cells. This intracellular residency establishes bacterial reservoirs as sources of chronic infection. Bacteria that persist intracellularly can convert phenotypically so that upon release from aged cells, the population is able to invade new host cells more aggressively. This passage from older cells into new cells is believed to contribute to chronic, recurrent infection. Taken together, findings that ML 141 limits populations of persisting bacteria with limited cytotoxic or bactericidal activity points to the possible usefulness of targeting CDC42 to augment current therapeutic approaches for chronic, recurrent infection.

RSM series as inhibitory compounds for *Staphylococcus aureus* in endothelial cells The scope of this disclosure is to: 1) synthesize a series of ML 141 structural analogs; 2) assess these structural analogs using an invasion assay; and 3) characterize further the pharmacology of ML 141.

Experimental Section 3: Develop analogs to increase ML 141 efficacy and potency

Rationale

ML 141 demonstrates specificity for CDC42, yet compound usefulness may be limited by its solubility. The goal of this Section is to design and synthesize novel analogs with improved solubility that efficiently inhibit GTP-loading of CDC42 and *S. aureus* invasion. The modified analogs are based on the core structure ML 141 as illustrated in Scheme 0. Modifications will be made at specific locations on the core aromatics at the three and/or five positions of the pyrazoline core in an attempt to increase hydrophilicity. The aromatic pyridine heterocycles or ether and alcohol groups will increase aqueous solubility and these groups are shown as generic spheres.

Scheme 0

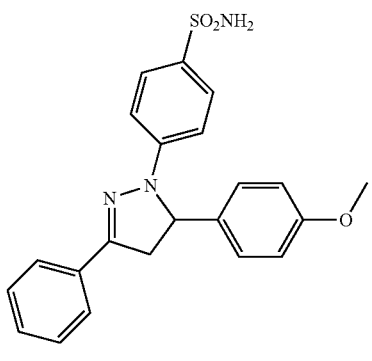

ML 141

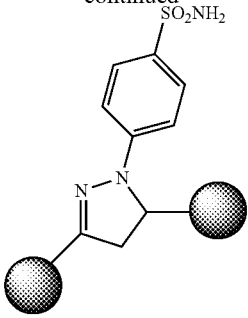

Modified Analogs

Study 1

Addition of Small Ether or Alcohol Groups or Larger Polyethylene Glycol Appendages to Specific Locations on the Core Aromatics in an Attempt to Increase Hydrophilicity.

The proposed synthesis commences with the reaction of 4-hydroxybenzaldehyde with alkylating agents such as 2-chloroethanol, 2-(2-chloroethoxy)ethanol, 2-[2-(2-chloroethoxy)ethoxy]ethanol (R=H) or their corresponding methyl ethers (R=CH$_3$) in sodium hydroxide. The resulting ether synthesis provides a more hydrophilic benzaldehyde as shown in Scheme 1. The attachment of the small ether or alcohol groups or larger polyethylene glycol appendages to the starting acetophenone has also been proven. The mixed aldol condensation of acetophenone and 4-methoxybenzaldehyde for the synthesis of ML 141 can be adapted for the construction of proposed analogs. Following literature precedent, the reaction of substituted acetophenones with substituted benzaldehydes will prepare the required chalcones as shown in Scheme 1. These chalcones will then be condensed and cyclized with 4-hydrazinobenzenesulfonamide, which is easily prepared as the hydrochloride salt from sulfanilamide. The appendages can be extended to a longer polyethylene glycol (PEG) substituent if desired. It is well known that the addition of PEG chains to organic compounds can increase aqueous solubility without fear to biological safety. The appendages can be extended to a PEG substituent. Indeed, several pharmaceutical drugs have made it to market or are currently in clinical trials with hydrophilic appendages.

Scheme 1 Design of ML 141 analogs with hydrophilic substituents attached to aromatic rings.

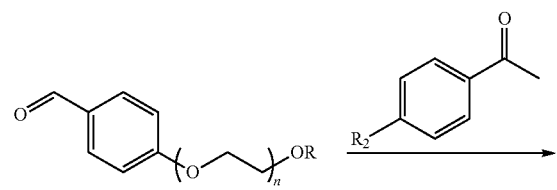

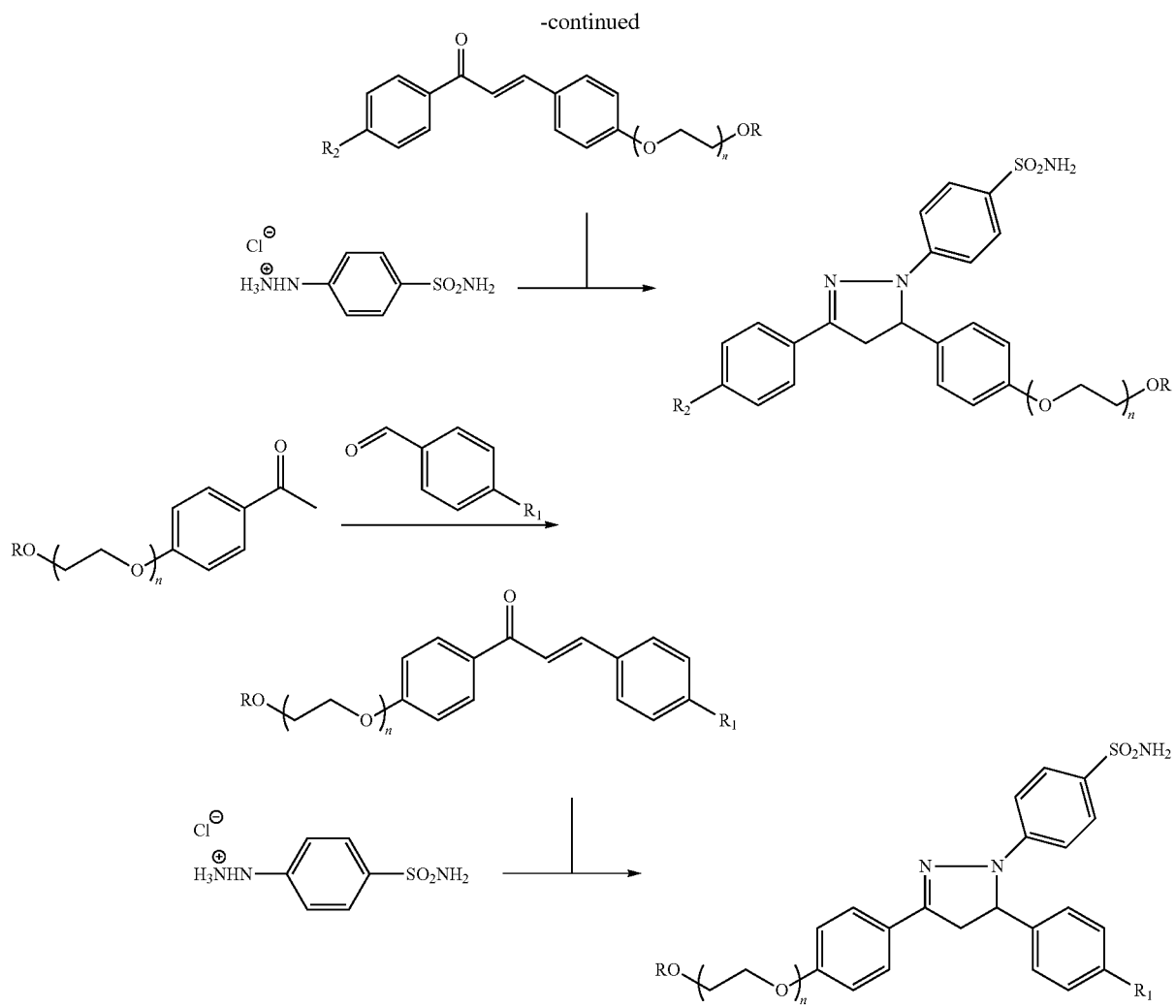

It is expected that replacement of the 4-methoxy substituent on the phenyl substituent at the five position of the pyrazoline with functionalized alkoxy substituents or addition of the functionalized alkoxy substituents to the phenyl moiety at the three position provides novel structural analogs of ML 141 with equivalent biological activity but improved solubility.

Results and Discussion

ML 141 Structural Analogs

The chemistry for the synthesis of ML 141 structural analogs is shown in Scheme 2. Hydrazine hydrochlorides are commercially available or prepared from their corresponding amines through diazotization followed by stannous chloride reduction. The prerequisite chalcones are prepared via aldol condensation from commercially available ketones with aromatic aldehydes. The general procedure is described as follows: the aldehyde (7.0 mmol) and ketone (7.0 mmol) are dissolved in ethanol (10-25 mL), the solution cooled to 0° C., and then 40% NaOH gradually added dropwise until precipitation commenced. The cold mixture is stirred until precipitation is complete and the product is then collected by vacuum filtration. The pyrazolines are synthesized as follows: the chalcone (1.0 mmol) and hydrazine hydrochloride (1.0 mmol) are dissolved in ethanol (25 mL) and a catalytic amount of sodium acetate is added (0.05 mmol). The reaction is then heated at reflux until determined complete by TLC (8-30 h). The solution is concentrated to half volume and then is cooled to produce solid product, which is then collected by vacuum filtration. If no solid is obtained, the remaining solvent is removed via rotoevaporation and the solid is taken up in ethyl acetate, washed with water, dried with sodium sulfate, filtered, and solvent evaporated to obtain crude product. Purification of crude product is achieved via recrystallization or column chromatography on silica gel.

Scheme 2: Synthesis of ML 141 structural analogs

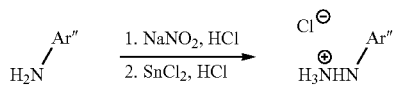

-continued

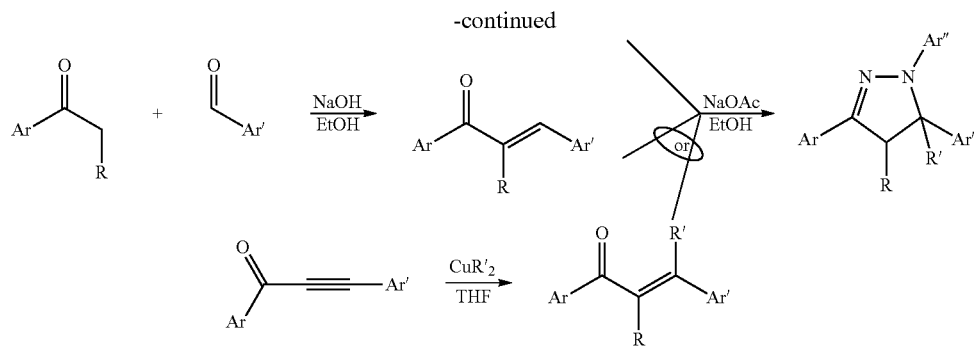

Structural analogs of ML 141 (RSM 04, 05, 06, 07, 11-18), shown in FIGS. 14A through 14L, are prepared specifically from p-sulfamylphenylhydrazine hydrochloride and the chalcones of methyl ketones and aromatic aldehydes as shown in Scheme 2. Structural analog RSM 19 is prepared from p-sulfamylphenylhydrazine hydrochloride and the chalcone of propiophenone and 4-methoxybenzaldehyde. The structural analogs are purified by standard means and characterized by IR and NMR spectroscopy.

ML 141 Structural Analogs Inhibit Host Cell Invasion

To examine whether structural analogs of ML 141 inhibit host cell invasion by *S. aureus*, HUVEC are incubated with structural analog compound (10 µM) or with an equimolar amount of ML 141 and are assayed against vehicle control treated infected samples. The examined structural analogs all inhibit host cell invasion as compared to the control (Tables 1 and 2), as shown by significantly lower mean fluorescence when compared to the PEG control.

Referring to Table 1, inhibition by RSM 05, RSM 06, RSM 07, RSM 11, RSM 12, RSM 13, RSM 17, RSM 19, RSM 20, RSM 21, and RSM 26 is similar to inhibition by ML 141. RSM 04, RSM 06, RSM 15, and RSM 16 inhibited invasion more than ML 141. RSM 05, RSM 15, and RSM 16 have GTP $IC_{50}$ concentrations in the same 2-4 µM range as ML 141, and RSM 07 and RSM 21 are only slightly higher.

Referring to Table 2, inhibition by RSM 27, RSM 28, RSM 29, RSM 30, RSM 31, RSM 32 and RSM 33 is similar to inhibition by ML 141.

TABLE 1

ML 141 structural analogs inhibit host cell invasion. Human umbilical vein endothelial cells (HUVEC) are incubated with ML 141 (10 µM), with ML 141 structural analogs (designated RSM 01-26; 10 µM), or with vehicle control polyethylene glycol (PEG, 1%), 18-20 hours prior to infection with fluorescently labeled *Staphylococcus aureus* (1 hour, 5% $CO_2$, 37° C.). Extracellular bacteria are removed using lysostaphin and gentamicin. Internalized bacteria are detected using flow cytometry (*less than vehicle control, †greater than ML 141, #less than ML 141, $p \leq 0.05$; ‡not different than ML 141, $p > 0.05$; n = 5/treatment). With regard to the GTP binding column, BODIPY-FL-GTP binding to CDC42 was assessed for a subset of the RSM series. For comparison, the reported $IC_{50}$ of ML 141 is 2-4 µM. Inhibition of BODIPY-FL-GTP binding to Rab7 was not detected when tested up to 100 µM.

| | Internalized bacteria (% control ± SEM) | | |
|---|---|---|---|
| | Structural analog | ML 141 | GTP binding ($IC_{50}$) |
| RSM 04 | 11 ± 1%*# | 35 ± 5%* | |
| RSM 05 | 38 ± 3%*‡ | 42 ± 3%* | 3.4 µM |
| RSM 06 | 23 ± 1%*# | 39 ± 5%* | 10.1 µM |
| RSM 07 | 34 ± 2%*‡ | 36 ± 3%* | 6.2 µM |

TABLE 1-continued

ML 141 structural analogs inhibit host cell invasion. Human umbilical vein endothelial cells (HUVEC) are incubated with ML 141 (10 µM), with ML 141 structural analogs (designated RSM 01-26; 10 µM), or with vehicle control polyethylene glycol (PEG, 1%), 18-20 hours prior to infection with fluorescently labeled *Staphylococcus aureus* (1 hour, 5% $CO_2$, 37° C.). Extracellular bacteria are removed using lysostaphin and gentamicin. Internalized bacteria are detected using flow cytometry (*less than vehicle control, †greater than ML 141, #less than ML 141, $p \leq 0.05$; ‡not different than ML 141, $p > 0.05$; n = 5/treatment). With regard to the GTP binding column, BODIPY-FL-GTP binding to CDC42 was assessed for a subset of the RSM series. For comparison, the reported $IC_{50}$ of ML 141 is 2-4 µM. Inhibition of BODIPY-FL-GTP binding to Rab7 was not detected when tested up to 100 µM.

| | Internalized bacteria (% control ± SEM) | | |
|---|---|---|---|
| | Structural analog | ML 141 | GTP binding ($IC_{50}$) |
| RSM 11 | 61 ± 2%*‡ | 57 ± 6%* | |
| RSM 12 | 57 ± 3%*‡ | 47 ± 4%* | |
| RSM 13 | 62 ± 5%*‡ | 63 ± 6%* | |
| RSM 14 | 71 ± 3%*† | 51 ± 3%* | |
| RSM 15 | 45 ± 1%*# | 53 ± 3%* | 2.2 µM |
| RSM 16 | 63 ± 4%*# | 89 ± 3%* | 3.7 µM |
| RSM 17 | 67 ± 8%*‡ | 66 ± 1%* | |
| RSM 18 | 76 ± 7%*† | 52 ± 3%* | |
| RSM 19 | 61 ± 2%*‡ | 58 ± 3%* | 13.5 µM |
| RSM 20 | 61 ± 4%*‡ | 50 ± 14%* | 46.5 µM |
| RSM 21 | 79 ± 3%*‡ | 61 ± 3%* | 5.5 µM |
| RSM 26 | 40 ± 3%*‡ | 58 ± 3%* | |

TABLE 2

ML141 and RSM structural analogs decrease intracellular infection. Human umbilical vein endothelial cells (HUVEC) were incubated (18-20 h) with ML141 (10 µmol/L), RSM structural analog (10 µmol/L), or dimethyl sulfoxide (DMSO), infected with *Staphylococcus aureus*, and extracellular bacteria removed using gentamicin and lysostaphin. Bacteria per host cell were counted in 100 cells from randomly selected fields using florescence microscopy.

| | Intracellular bacteria/cell (±SEM) | | |
|---|---|---|---|
| | Structural analog | ML 141 | DMSO |
| RSM 27 | 4.4 ± 0.5* | 3.4 ± 0.4* | 8.0 ± 0.8 |
| RSM 28 | 1.4 ± 0.3* | 1.6 ± 0.2* | 6.2 ± 0.8 |
| RSM 29 | 2.4 ± 0.4* | 1.6 ± 0.2* | 6.2 ± 0.8 |
| RSM 30 | 1.7 ± 0.3* | 1.2 ± 0.3* | 7.3 ± 0.8 |
| RSM 31 | 1.4 ± 0.4* | 1.2 ± 0.3* | 7.3 ± 0.8 |
| RSM 32 | 5.5 ± 0.4* | 5.6 ± 0.4* | 10.7 ± 0.8 |
| RSM 33 | 5.4 ± 0.4* | 5.6 ± 0.4* | 10.7 ± 0.8 |

*Less than DMSO control by one-way ANOVA followed by Newman-Keuls multiple comparison test.

TABLE 3

Molecular structure of ML 141 and related RSM pyrazoline analogs.

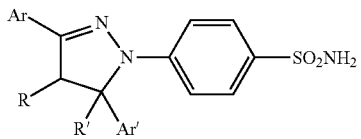

| ID | Ar | R | Ar' | R' |
|---|---|---|---|---|
| ML 141 | Ph | H | 4-MeOPh | H |
| RSM 04 | 4-MeOPh | H | 4-ClPh | H |
| RSM 05 | Ph | H | 3,4-(OCH$_2$O)Ph | H |
| RSM 06 | 4-MeOPh | H | 3,4-(OCH$_2$O)Ph | H |
| RSM 07 | 4-MeOPh | H | Ph | H |
| RSM 11 | Ph | H | 4-MeOCH$_2$CH$_2$OPh | H |
| RSM 12 | 4-MeOPh | H | 4-MeOCH$_2$CH$_2$OPh | H |
| RSM 13 | Ph | H | 3,4,5-MeOPh | H |
| RSM 14 | 4-MeOPh | H | 3,4,5-MeOPh | H |
| RSM 15 | Ph | H | 3,4-MeOPh | H |
| RSM 16 | 4-MeOPh | H | 3,4-MeOPh | H |
| RSM 17 | 4-MeOCH$_2$CH$_2$OPh | H | 4-MeOPh | H |
| RSM 18 | 4-MeOCH$_2$CH$_2$OPh | H | 4-MeOCH$_2$CH$_2$OPh | H |
| RSM 19 | Ph | Me | 4-MeOPh | H |
| RSM 20 | 4-MeOCH$_2$CH$_2$OPh | H | 4-ClPh | H |
| RSM 21 | Ph-(2-CH$_2$)— | | 4-MeOPh | H |
| RSM 26 | Ph | H | 4-MeOPh | Me |
| RSM 27[#] | Ph | — | 4-MeOPh | — |
| RSM 28 | Ph | H | 4-Me$_2$NPh | H |
| RSM 29 | Ph | H | 4-MeCONHPh | H |
| RSM 30 | 3-MeCONHPh | H | 4-MeOPh | H |
| RSM 31 | 4-MeCONHPh | H | 4-MeOPh | H |
| RSM 32 | 4-EtCONHPh | H | 4-MeOPh | H |
| RSM 33 | 3-EtCONHPh | H | 4-MeOPh | H |

[#]RSM 27 is acyclic hydrazine in place of pyrazoline:

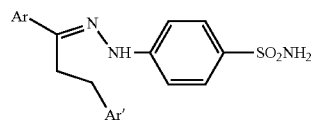

TABLE 4

Assessment of cytotoxicity. Human umbilical vein endothelial cells were pretreated (18-20 h) with vehicle control, with ML 141 (10 μM), or with structural analog at equimolar concentration and viability assessed by propidium iodide (PI) exclusion (**greater than vehicle control, $p < 0.01$ by Student's t-test; n = 3/treatment).

| | Mean fluorescence intensity ($\times 10^4 \pm$ SEM) | |
|---|---|---|
| | Vehicle control | Compound (10 μM) |
| ML 141 | 1.7 ± 0.1 | 2.1 ± 0.3 |
| RSM 04 | 1.9 ± 0.2 | 4.6 ± 0.2** |
| RSM 05 | 2.6 ± 0.8 | 3.9 ± 0.2 |
| RSM 06 | 2.4 ± 0.3 | 2.8 ± 0.1 |
| RSM 07 | 1.5 ± 0.8 | 2.5 ± 0.4 |
| RSM 15 | 3.6 ± 0.8 | 4.0 ± 0.4 |
| RSM 16 | 1.9 ± 0.2 | 1.4 ± 0.2 |
| RSM 19 | 2.0 ± 0.3 | 2.6 ± 0.01 |
| RSM 20 | 2.6 ± 0.8 | 2.1 ± 0.2 |
| RSM 21 | 2.4 ± 0.3 | 2.8 ± 0.09 |
| RSM 26 | 13.3 ± 1.5 | 26.8 ± 2.1** |

TABLE 5

Assessment of cytotoxicity. RAW 264.7 cells were plated and treated as described for the invasion assay (Table 2). Following pretreatment (18-20 h), RAW cells were lifted from plates using cell scrapers, washed extensively in FACS buffer, incubated briefly with propidium iodide (Sigma-Aldrich, 0.5 mg/mL), and fluorescence detected immediately using an Accuri C6 flow cytometer.

| | Mean fluorescence intensity ($\times 10^3 \pm$ SEM) | |
|---|---|---|
| | Vehicle control | Compound (10 μM) |
| ML 141 | 2.2 ± 0.2 | 2.5 ± 0.3 |
| RSM 27 | 1.1 ± 0.0 | 1.0 ± 0.1 |
| RSM 28 | 9.8 ± 1.2 | 11 ± 2.0 |
| RSM 29 | 3.1 ± 0.7 | 4.2 ± 0.3 |
| RSM 30 | 2.9 ± 0.5 | 2.4 ± 0.4 |
| RSM 31 | 1.6 ± 0.1 | 2.4 ± 0.3 |
| RSM 32 | 1.3 ± 0.1 | 2.8 ± 1.1 |
| RSM 33 | 1.3 ± 0.1 | 2.9 ± 1.1 |

TABLE 6

Assessment of bactericidal activity. $1.2 \times 10^8$ colony forming units (CFU) of Staphylococcus aureus were incubated with compound or with vehicle control in human umbilical vein endothelial cell media (1 h, 5% CO$_2$, 37° C.). Serial dilutions were plated onto tryptic soy agar, incubated (18-20 h, 37° C.), colonies enumerated, and CFU/ml determined (*less than control, $p < 0.05$ by Student's t-test, n = 3/treatment).

| | CFU ($\times 10^8 \pm$ SEM) | |
|---|---|---|
| | Vehicle control | Compound (10 μM) |
| ML 141 | 9.8 ± 1.5 | 8.8 ± 2.9 |
| RSM 04 | 6.0 ± 1.3 | 3.8 ± 0.8 |
| RSM 05 | 12.1 ± 0.5 | 8.0 ± 1.7 |
| RSM 06 | 3.4 ± 0.5 | 4.9 ± 1.6 |
| RSM 07 | 13.8 ± 1.6 | 11.5 ± 1.1 |
| RSM 15 | 9.0 ± 0.6 | 10.1 ± 1.0 |
| RSM 16 | 8.6 ± 0.2 | 8.9 ± 1.9 |
| RSM 19 | 10.7 ± 0.6 | 9.4 ± 1.0 |
| RSM 20 | 12.5 ± 0.6 | 10.0 ± 0.2 |
| RSM 21 | 15.0 ± 1.1 | 15.0 ± 1.1 |
| RSM 26 | 9.8 ± 1.1 | 0.8 ± 1.1* |

TABLE 7

Assessment of bactericidal activity. $3.2 \times 10^6$ colony forming units (CFU) of Staphylococcus aureus were incubated with compound (ML 141 or analog) or with vehicle control in Dulbecco's Modified Eagle's Medium supplemented with 10% fetal bovine serum (1 h, 5% CO$_2$, 37° C.). Serial dilutions were plated onto tryptic soy agar, incubated (18-20 h, 37° C.) colonies enumerated, and CFU/ml determined ($p < 0.05$ by Student's t-test, n = 3-5/treatment).

| | CFU/mL ($\times 10^9 \pm$ SEM) | |
|---|---|---|
| 20 mM | Vehicle control | Compound |
| ML141 | 0.9 ± 0.07 | 0.9 ± 0.09 |
| RSM 27 | 2.6 ± 0.2 | 2.4 ± 0.6 |
| RSM 28 | 1.5 ± 0.07 | 1.8 ± 0.05 |
| RSM 29 | 1.3 ± 0.3 | 1.4 ± 0.1 |
| RSM 30 | 1.4 ± 0.1 | 1.5 ± 0.02 |
| RSM 31 | 1.3 ± 0.2 | 0.9 ± 0.09 |
| RSM 32 | 2.7 ± 0.2 | 2.4 ± 0.3 |
| RSM 33 | 1.4 ± 0.2 | 1.3 ± 0.04 |

Depolymerization of Actin Stress Fibers During Infection is Limited by ML 141

Figure 8A:
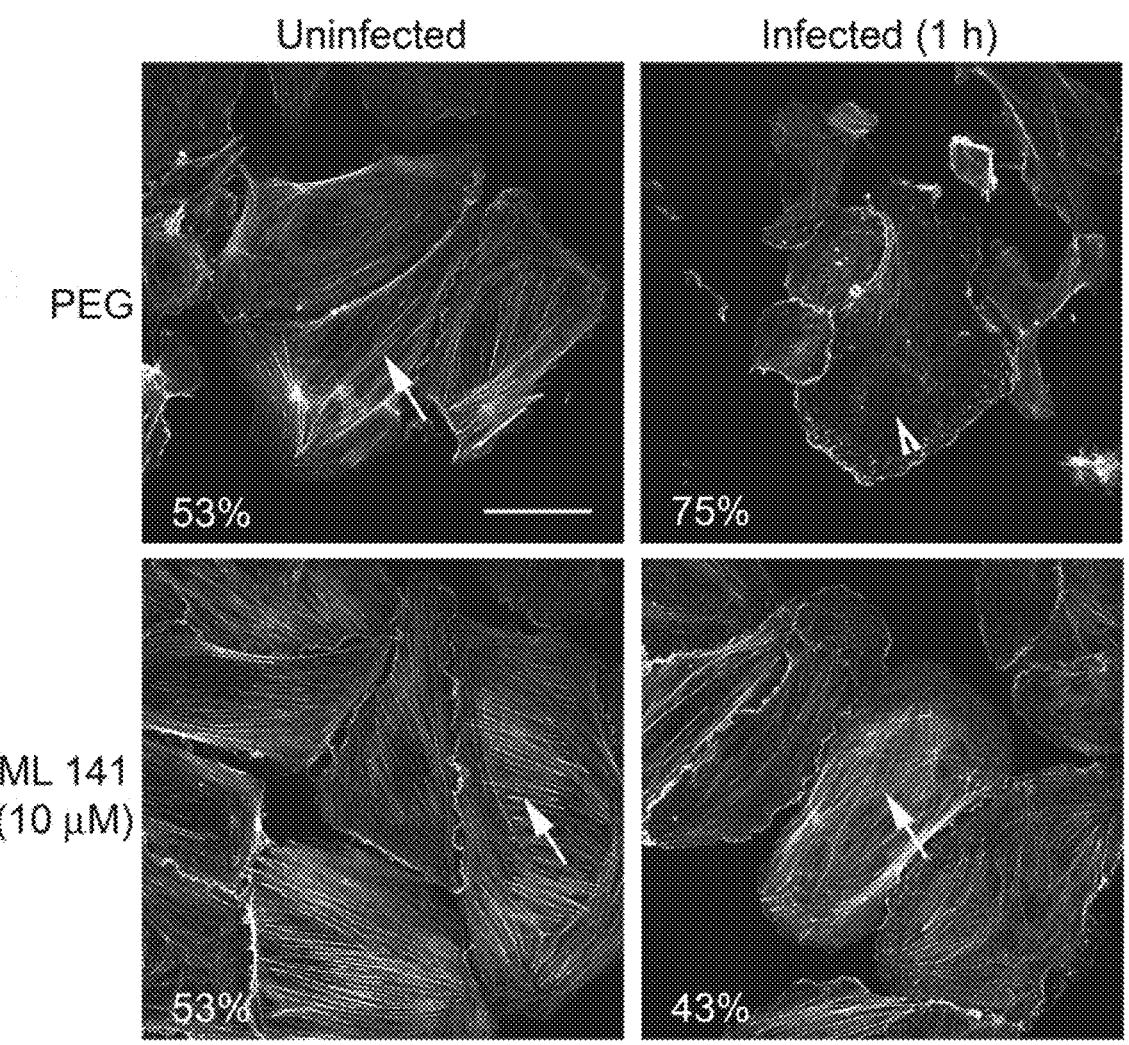
FIG. 8A is an image depicting ML 141 limiting actin stress fiber depolymerization during infection. Human umbilical vein endothelial cells (HUVEC) were incubated with ML 141 or with the vehicle control polyethylene glycol (PEG) 18-20 h prior to infection with *Staphylococcus aureus* (1 h). Actin was detected using Alexa Fluor 488 phalloidin. Arrows indicate intact actin stress fibers. Arrowhead indicates cell lacking actin stress fibers. 100 cells/treatment were evaluated from randomly selected fields. Data are presented as the % of cells in which actin stress fibers were not detected. Scale bar is 50 µm.
Figure 8B:
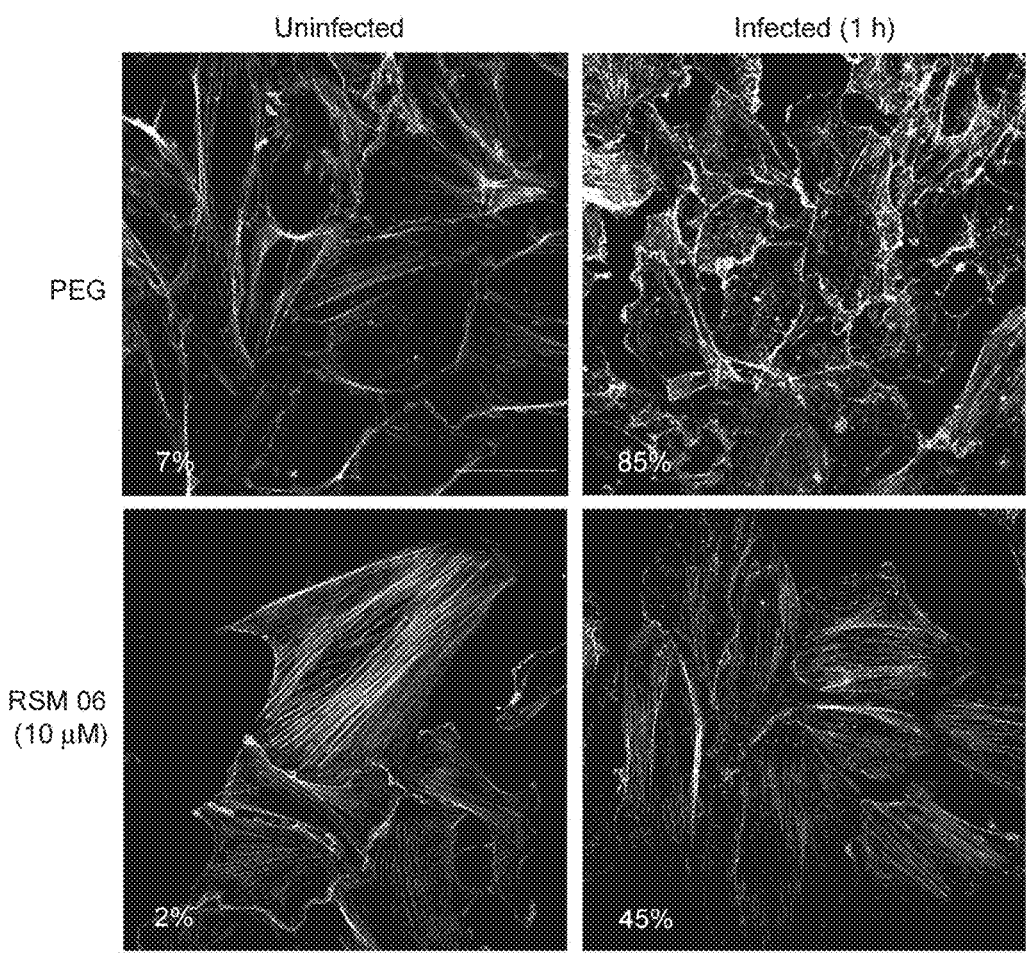
FIG. 8B is an image depicting RSM 06 limiting actin stress fiber depolymerization during infection. Human umbilical vein endothelial cells (HUVEC) were incubated with RSM 06 or with the vehicle control polyethylene glycol (PEG) 18-20 h prior to infection with *Staphylococcus aureus* (1 h). Actin was detected using Alexa Fluor 488 phalloidin. 200 cells/treatment were evaluated from randomly selected fields. Data are presented as the % of cells in which actin stress fibers were not detected. Scale bar is 50 µm.
Figure 8C:
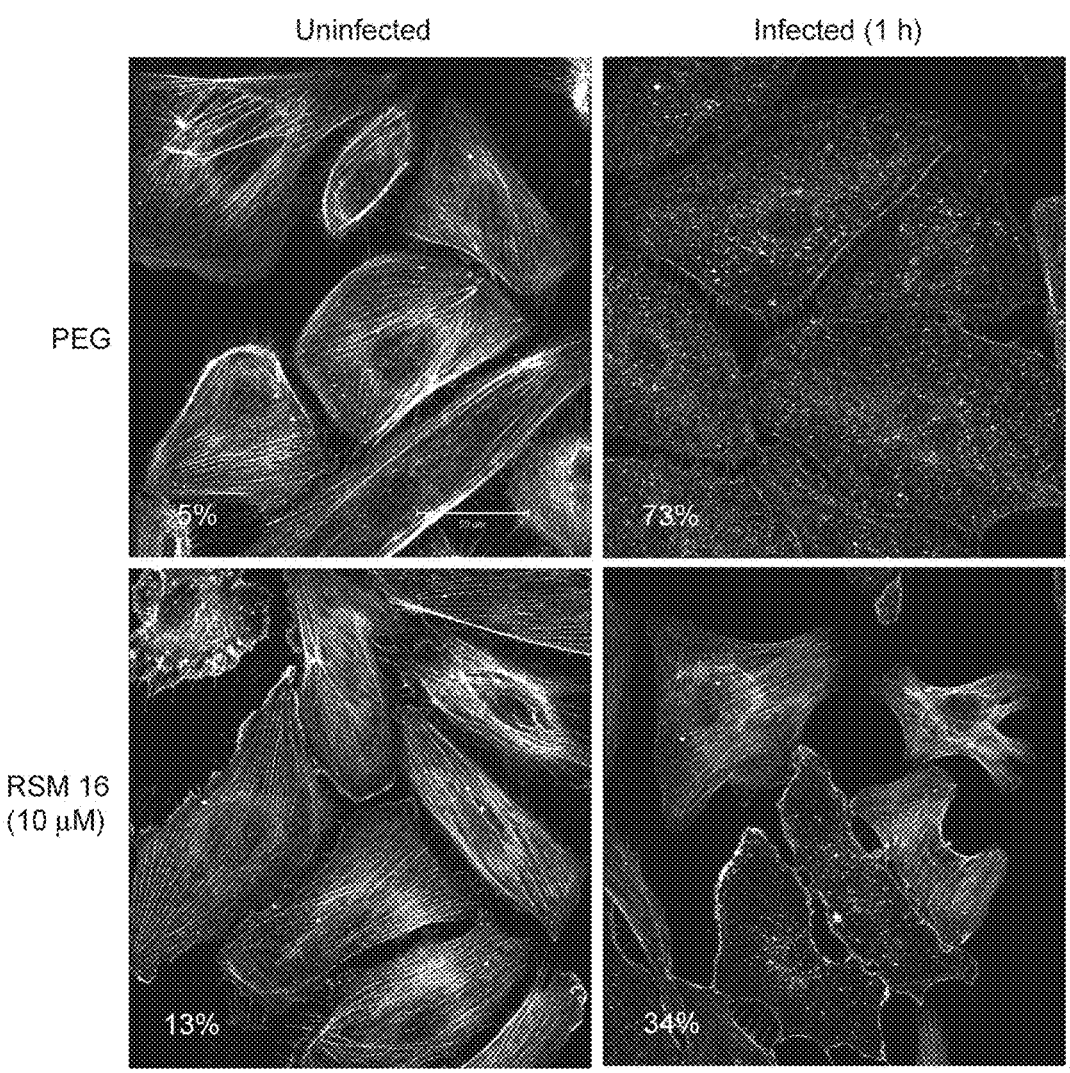
FIG. 8C is an image depicting RSM 16 limiting actin stress fiber depolymerization during infection. Human umbilical vein endothelial cells (HUVEC) were incubated with RSM 16 or with the vehicle control polyethylene glycol (PEG) 18-20 h prior to infection with *Staphylococcus aureus* (1 h). Actin was detected using Alexa Fluor 488 phalloidin. 200 cells/treatment were evaluated from randomly selected fields. Data are presented as the % of cells in which actin stress fibers were not detected. Scale bar is 50 µm.

When actin stress fibers depolymerize, the actin monomers reorganize at the cell membrane to facilitate endocytic uptake. The process appears to be partially regulated by the small GTPase CDC42, indicated by the finding that in cells lacking active CDC42, depolymerization is limited as is endocytic uptake. Research had found previously that host cell invasion by *S. aureus* stimulates the depolymerization of actin stress fibers. Inhibition of this depolymerization by LY294002, an inhibitor of phosphoinositide 3-kinase activity, was associated with decreased invasion, suggesting that the depolymerization of stress fibers and redistribution of actin at the cell membrane facilitates invasion. Next was examined whether the specific inhibition of CDC42 using ML 141 would limit depolymerization during infection. In response to infection, stress fibers depolymerized in 75% of vehicle treated cells yet remained intact in ML 141 treated cells (FIG. 8). This finding indicates that ML 141 blunts the depolymerization of actin stress fibers during infection. The finding suggests that an underlying mechanism for ML 141 inhibition of invasion is due in part to the limited redistribution of actin required for endocytic uptake of pathogenic *S. aureus*. Two of the ML 141 derivatives were selected to evaluate whether either compound limited the redistribution of actin. Both RSM 06 and RSM 16 limited actin depolymerization during invasion. These findings suggest that the inhibition of invasion by RSM 6 and by RSM 16 is due in part to the limited redistribution of actin.

Implications

ML 141 and its structural analogs provide a unique tool for exploring the role of CDC42 in mediating host cell invasion. Taken together, the investigation into ML 141 and its structural analogs has the potential to provide evidence that supports future compound development for the treatment of invasive infection. Alternatively, findings may open new directions for research into the role of this small-GTPase in host immune responses. Either outcome will impact the evaluation of treatment strategies that address infection at the level of the host, elucidate cellular processes under the regulation of CDC42, and expand upon the characterization of ML 141 and its structural analogs.

NMR Data

RSM 04

$^1$H NMR (300 MHz, CDCl$_3$) δ 3.14 (dd, J=5.8 Hz, 17.0 Hz, 1H), 3.85 (s, 3H), 3.88 (dd, J=12.1 Hz, J=17.0 Hz, 1H), 4.59 (s, 2H), 5.31 (dd, J=5.8 Hz, 12.1 Hz), 6.93 (d, J=12.4 Hz, 2H), 7.03 (d, J=9.1 Hz, 2H), 7.19 (d, J=8.6 Hz, 2H), 7.31 (d, J=8.6 Hz, 2H), 7.67 (d, J=4.7 Hz, 2H), 7.69 (d, J=5.0 Hz, 2H)

RSM 05

$^1$H NMR (300 MHz, CDCl$_3$) δ 3.11 (dd, J=5.8 Hz, 17.6 Hz, 1H), 3.80 (dd, J=12.1 Hz, 17.6 Hz, 1H), 5.22 (dd, J=5.8 Hz, 12.1 Hz, 1H), 5.53 (s, 2H), 5.86 (s, 2H), 6.61 (s, 1H), 6.69 (s, 2H), 7.02 (d, J=8.3 Hz, 2H), 7.40-7.34 (m, 3H), 7.69-7.65 (m, 4H)

RSM 06

$^1$H NMR (300 MHz, CDCl$_3$) δ 3.16 (dd, J=5.8 Hz, 17.3 Hz, 1H), 3.83 (dd, J=12.4 Hz, 17.3 Hz, 1H), 3.85 (s, 3H), 5.24 (dd, J=5.8 Hz, 12.4 Hz, 1H), 5.93 (s, 2H), 6.67 (s, 1H), 6.76 (s, 2H), 6.93 (d, J=9.1 Hz, 2H), 7.07 (d, J=9.1 Hz, 2H), 7.67 (d, J=4.5 Hz, 2H), 7.69 (d, J=4.5 Hz, 2H)

RSM 07

$^1$H NMR (300 MHz, DMSO-D$_6$) δ 3.16 (dd, J=5.0 Hz, 17.6 Hz, 1H), 3.80 (s, 3H), 3.95 (dd, J=12.1 Hz, 17.6 Hz, 1H), 5.60 (dd, J=5.0 Hz, 12.1 Hz, 1H), 7.06-6.99 (m, 6H), 7.39-7.26 (m, 5H), 7.57 (d, J=9.1 Hz, 2H), 7.74 (d, J=8.8 Hz, 2H)

RSM 11

$^1$H NMR (400 MHz, CDCl$_3$) δ 3.18 (dd, J=17.2 Hz, 5.9 Hz, 1H), 3.42 (s, 3H), 3.71 (t, J=4.8 Hz, 2H), 3.86 (dd, J=17.6 Hz, 12.6 Hz 1H), 4.06 (t, J=4.8 Hz, 2H) 4.69 (s, 2H), 5.30 (dd, J=12.1 Hz, 5.8 Hz, 1H), 6.86 (d, J=8.4 Hz, 2H), 7.07 (d, J=8.8 Hz, 2H), 7.15 (d, J=8.8 Hz, 2H), 7.35-7.43 (m, 3H), 7.67 (d, J=8.8 Hz, 2H), 7.73 (dd, J=7.6 Hz, 1.4 Hz, 2H)

RSM 12

$^1$H NMR (400 MHz, CDCl$_3$) δ 3.16 (dd, J=17.3 Hz, 5.8 Hz, 1H), 3.43 (s, 3H), 3.72 (t, J=5.0 Hz, 2H) 3.79-3.89 (m, 4H), 4.08 (t, J=4.7 Hz, 2H), 4.59 (s, 2H), 5.28 (dd, J=12.1 Hz, 5.8 Hz, 1H), 6.91 (dd, J=15.7 Hz, 8.8 Hz, 4H), 7.05 (d, J=8.8 Hz, 2H), 7.16 (d, J=8.5 Hz, 2H), 7.68 (dd, J=9.1 Hz, 4.1 Hz, 4H)

RSM 13

$^1$H NMR (300 MHz, CDCl$_3$) δ 3.23 (dd, 6.6 Hz, 17.6 Hz, 1H), 3.80 (s, 6H), 3.83 (s, 3H), 3.89 (dd, J=12.4 Hz, 17.6 Hz, 1H), 5.25 (dd, J=6.6 Hz, 12.4 Hz, 1H), 6.46 (s, 2H), 7.12 (d, J=8.8 Hz, 2H), 7.47-7.41 (m, 3H), 7.78-7.74 (m, 4H)

RSM 14

$^1$H NMR (300 MHz, CDCl$_3$) δ 3.20 (dd, J=6.6 Hz, 17.6 Hz, 1H), 3.80 (s, 6H), 3.83 (s, 3H), 3.85 (s, 3H), 3.85 (dd, J=12.1 Hz, 17.6 Hz, 1H), 5.21 (dd, J=6.6 Hz, 12.1 Hz, 1H), 6.46 (s, 2H), 6.94 (d, J=9.6 Hz, 2H), 7.09 (d, 8.8 Hz, 2H)

RSM 15

$^1$H NMR (300 MHz, DMSO-D$_6$) δ 3.19 (dd, J=5.5 Hz, 17.6 Hz, 1H), 3.69 (s, 3H) 3.72 (s, 3H), 3.94 (dd, J=12.1 Hz, 17.6 Hz, 1H), 5.54 (dd, J=5.5 Hz, 12.1 Hz, 1H), 6.69-6.67 (m, 1H), 6.88 (d, J=8.1 Hz, 1H), 6.94 (d, J=2.1 Hz, 1H), 7.09 (d, J=8.6 Hz, 2H), 7.48-7.39 (m, 3H), 7.59 (d, J=9.2 Hz, 2H), 7.79 (d, J=6.6 Hz, 2H)

RSM 16

$^1$H NMR (300 MHz, DMSO-D$_6$) δ 3.15 (dd, J=5.5 Hz, 17.6 Hz, 1H), 3.68 (s, 3H) 3.71 (s, 3H), 3.79 (s, 3H), 3.89 (dd, J=12.1 Hz, 17.6 Hz, 1H), 5.84 (dd, J=5.5 Hz, 12.1 Hz, 1H), 6.68-6.67 (m, 1H), 6.87 (d, J=8.1 Hz, 1H), 6.93 (d, J=2.1 Hz, 1H), 7.07-6.99 (m, 6H), 7.57 (d, J=9.2 Hz, 2H), 7.72 (d, J=7.8 Hz, 2H)

RSM 17

$^1$H NMR (400 MHz, CDCl$_3$) δ 3.15 (dd, J=17.6 Hz, 5.8 Hz, 1H), 3.46 (s, 3H), 3.75-3.78 (m. 5H), 3.83 (dd, J=17.2 Hz, 12.1 Hz, 1H), 4.15 (t, J=4.8 Hz, 2H), 4.60 (s, 2H), 5.28 (dd, J=12.1 Hz, 5.5 Hz, 1H), 6.85 (d, J=8.4 Hz, 2H), 6.95 (d, J=8.8 Hz, 2H), 7.05 (d, J=8.8 Hz, 2H), 7.16 (d, J=8.4 Hz, 2H), 7.67 (d, J=8.8 Hz, 4H)

RSM 18

$^1$H NMR (400 MHz, CDCl$_3$) δ 3.15 (dd, J=17.2 Hz, 5.9 Hz, 1H), 3.43 (s, 3H), 3.46 (s, 3H), 3.72 (t, J=4.8 Hz, 2H) 3.77 (t, J=4.8 Hz, 2H) 3.83 (dd, J=17.2 Hz, 12.1 Hz, 1H), 4.08 (t, J=4.8 Hz, 2H), 4.15 (t, J=4.4 Hz, 2H), 4.62 (s, 2H), 5.27 (dd, J=12.1 Hz, 5.9 Hz, 1H), 6.88 (d, J=8.8 Hz, 2H), 6.96 (d, J=8.8 Hz, 2H), 7.05 (d, J=8.8 Hz, 2H), 7.15 (d, J=8.8 Hz, 2H), 7.67 (dd, J=9.2 Hz, 2.6 Hz, 4H)

RSM 19

$^1$H NMR (400 MHz, CDCl$_3$) δ 0.84 (d, J=7.7 Hz, 3H), 3.81 (s, 3H), 3.99-4.08 (m, 1H), 4.64 (s, 2H) 5.30 (d, J=11.4 Hz, 1H) 6.87-6.90 (m, 2H), 7.08 (d, J=8.8 Hz, 2H), 7.14-7.15 (m, 2H), 7.36-7.45 (m, 3H), 7.67 (d, J=8.8 Hz, 2H), 7.77 (dd, J=8.4 Hz, 1.5 Hz, 2H)

RSM 20

$^1$H NMR (400 MHz, CDCl$_3$) δ 3.15 (dd, J=17.2 Hz, 5.9 Hz, 1H), 3.47 (s, 3H), 3.77 (t, J=4.8 Hz, 2H), 3.87 (dd, J=17.2 Hz, 12.1 Hz, 1H) 4.16 (t, J=4.4 Hz, 2H), 4.60 (s, 2H), 5.31 (dd, J=12.1 Hz, 5.9 Hz, 1H), 6.96 (d, J=8.8 Hz, 2H), 7.03 (d, J=9.2 Hz, 2H), 7.19 (d, J=8.4 Hz, 2H), 7.31 (d, J=8.4 Hz, 2H), 7.68 (t, J=9.2, 4H). 13C NMR (100 MHz, DMSO-de) δ 43.5, 56.6, 58.8, 62.1, 67.7, 70.9, 112.4, 115.3, 124.9, 127.8, 128.3, 129.6, 132.7, 133.4, 141.3, 146.5, 150.2, 160.1

RSM 21

$^1$H NMR (400 MHz, CDCl$_3$) δ 2.23 (dd, J=16.1 Hz, 7.7 Hz, 1H), 2.91 (dd, J=15.7 Hz, 9.2 Hz, 1H), 3.72 (s, 3H), 4.18-4.24 (m, 1H), 4.61 (s, 2H), 5.55 (d, J=11.0 Hz, 1H), 6.75-6.77 (m, 2H), 6.94-7.03 (m, 4H), 7.21 (d, J=6.1 Hz, 1H), 7.28-7.34 (m, 2H), 7.67 (d, J=9.2 Hz, 2H), 7.76 (d, J=8.4 Hz, 1H). 13C NMR (100 MHz, DMSO-$d_6$) δ 54.8, 55.5, 56.7, 66.9, 112.6, 114.8, 122.7, 126.8, 127.2, 127.7, 128.3, 131.0, 133.1, 147.5, 152.2, 159.2, 164.2

RSM 26

$^1$H NMR (300 MHz, CDCl$_3$) δ 1.87 (s, 3H), 3.47 (s, 2H), 3.82 (s, 3H), 4.60 (s, 2H), 6.90 (d, J=8.8 Hz, 2H), 7.06 (d, J=9.1 Hz, 2H), 7.45-7.31 (m, 5H), 7.62 (d, J=9.1 Hz, 2H), 7.73 (d, J=9.6 Hz, 2H)

Experimental Section 4: Inhibition of CDC42 Limits *S. aureus* Infection

Rationale

Selective small molecule inhibition of CDC42 may disrupt cellular processes used by *S. aureus* to gain host cell entry and is a druggable target in the treatment of invasive infection.

Materials and Methods

Reagents.

Reagents were used at the concentrations and durations indicated within each figure legend or method described below: human fibronectin (Sigma-Aldrich, St. Louis, Mo.); all remaining reagents were sourced as described in Experimental Section 1 above.

Structural Analog Synthesis.

General procedure for pyrazolines known as RSM structural analogs (Bashir et al., 2011). Equimolar equivalents of the corresponding chalcone (see below) and p-sulfamylphenylhydrazine hydrochloride were dissolved in 95% ethanol (25 mL/mmol) and a catalytic amount of sodium acetate was added. The mixture was then refluxed for 24 hr. The reaction mixture was concentrated to about ⅓ of the volume via simple distillation. The reaction was then cooled to room temperature and the product was isolated via vacuum filtration. When necessary, the product was recrystallized with ethanol or purified by flash chromatography on silica gel.

General Procedure for Chalcone Synthesis.

The corresponding benzaldehyde (1.0 equiv.) and the corresponding acetophenone (1.0 equiv.) derivatives were dissolved in 95% ethanol (1.5 mL/mmol) and cooled to 0° C. in an ice bath. A solution of 40% sodium hydroxide (up to 0.5 mL/mmol) was then slowly added drop wise over 1 h or until solid begins to precipitate. The mixture was left to stir at 0° C. for another 30 min and the product was isolated via vacuum filtration. The crude solid was washed with cold 95% ethanol and was recrystallized using 95% ethanol. Chalcone used for the preparation of RSM 26 was prepared via cuprate addition to the conjugated ynone.

General Procedure for Alkylation of Phenols.

4-Hydroxyacetopheone or 4-hydroxybenzaldehyde (1.00 equiv.) was added to a solution of 2-chloroethyl methyl ether or 2-(2-tosylethoxy)ethyl methyl ether (1.20 equiv.) and potassium carbonate (1.20 equiv.) in DMF (1.5 mL/mmol). The reaction mixture was heated to 60° C. and left to stir for 16 hours. To the cooled mixture was added water (30 mL) and extracted with ethyl acetate (3×30 mL). The combined organic layers were then washed with 1M NaOH (1×30 mL) water (3×30 mL) and brine (1×30 mL) and dried over magnesium sulfate. The solvent was removed in vacuo.

Transmission Electron Microscopy.

HUVEC were plated onto glass coverslips at 3×10/ml, pretreated and infected at a multiplicity of infection (MOI) of 30 for 2 h. Extracellular bacteria were removed and cells incubated for an additional 24 h in media containing antibiotics. Cells were immersion fixed with 2.5% glutaraldehyde/2.0% paraformaldehyde/2 mM calcium/1 mM magnesium (15 min, twice), washed extensively with PBS, post-fixed with 1.0% osmium tetroxide/1.5% potassium ferrocyanide in 0.1 M sodium cacodylate buffer, dehydrated in a graded ethanol series followed by propylene oxide, and embedded in EMBed812 (Electron Microscopy Sciences). Serial ultrathin sections were cut, collected onto Pioloform slot grids, and counterstained with aqueous uranyl acetate and Reynold's lead citrate (30 min each). Electron micrographs were obtained at 120 KV using a JEOL JEM-1400 equipped with a Gatan Ultrascan 1000XP camera.

Flow Cytometry.

To examine β1 surface expression, recycling of the integrin was terminated (4° C., 15 min) and HUVEC lifted from plates using cell scrapers. After washing in FACS buffer (2% BSA/0.1% sodium azide/PBS), cells were incubated with PE-conjugated anti-β1 (BD; 30 min, on ice), washed, fixed in FACS buffer containing 4% paraformaldehyde, and analyzed using an Accuri C6 flow cytometer (BD).

Fibronectin Adhesion Assay.

HUVEC were plated and pretreated as described for the invasion assay. 96-well, non-tissue culture treated plates (Sarstedt, Newton, N.C.) were coated with fibronectin (20 µg/ml; 2 h; 37° C.), washed with PBS, and blocked with bovine serum albumin (2%, 30 min, RT). HUVEC were lifted from the 35 mm dishes using cell scrapers, 100 µl counted for normalization using the Accuri C6, and 200 µl transferred to the 96-well plate (2 h, 5% CO$_2$, 37° C.). After extensive washes in PBS, cells were removed from the plate using trypsin, washed in FACS buffer, fixed, and 100 µl counted. These cell counts were normalized to those that had been taken prior to plating on the fibronectin-coated plate.

Methods not explicitly described in Experimental Section 4 were performed as described in Experimental Section 1.

Results and Discussion

Small Molecule Inhibition of CDC42 Limits Host Cell Invasion by *S. aureus*.

Figure 11:
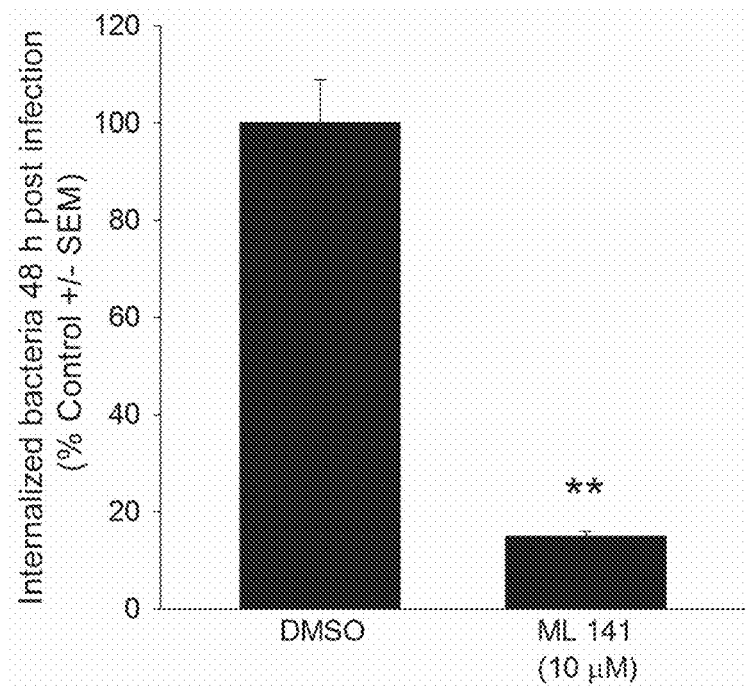
FIG. 11 is a graph illustrating suppression of intracellular population sustained over time. Human umbilical vein endothelial cells (HUVEC) were pretreated (10 μM, 18 hours) with the vehicle control dimethyl sulfoxide (DMSO) or ML 141 and infected with *Staphylococcus aureus* (1 hour). At 48 hours, intracellular bacteria were recovered, serial dilutions incubated on tryptic soy agar and colonies enumerated. Data are presented as % control, ±SEM (*less than vehicle control; p≤0.05 by t-test; n=3-5/treatment).

HUVEC were incubated with 10 µM ML 141, a recently characterized inhibitor with selectivity for the active site of human CDC42, or with the vehicle control polyethylene glycol (PEG, 18-20 h) followed by incubation with an invasive strain of *S. aureus* (ATCC 29213). ML 141 decreased invasion at 1 h (FIGS. 4A-1 and 4A-2). Inhibition was detectable in all cell types examined (HEK 293A, U-87 MG, RAW 264.7, and A549; data not shown). To examine whether the intracellular bacterial population within ML 141 treated host cells returned to control levels over time, intracellular bacteria were examined 48 h post-invasion. The number of viable bacteria recovered at 48 h was lower in ML 141 treated cells compared to vehicle control (FIGS. 7 and 11).

Small Molecule Inhibition of CDC42 Limits Damage to Host Cells.

Figure 9:
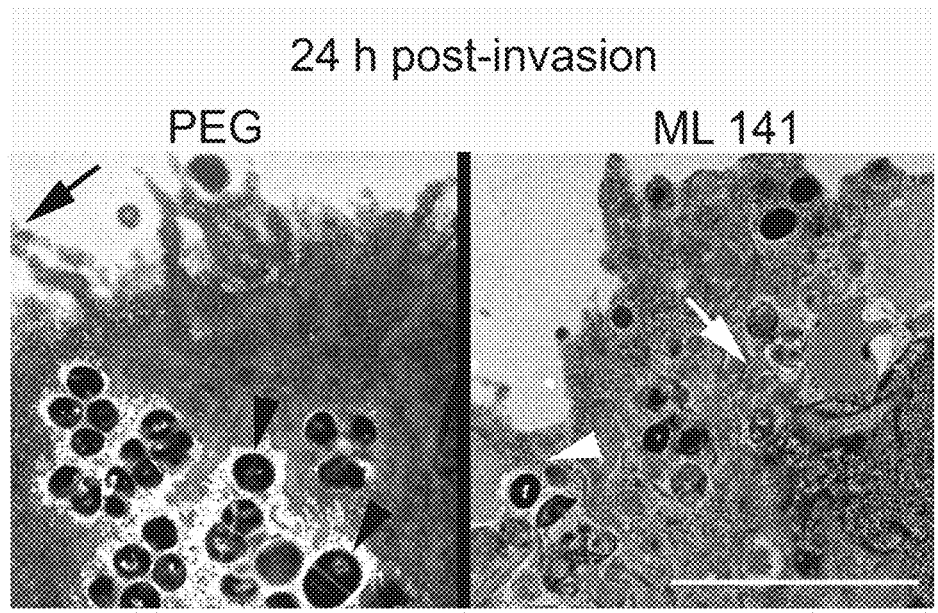
FIG. 9 is an image depicting ML 141 limiting damage to host cells. Human umbilical vein endothelial cells were incubated with the vehicle control polyethylene glycol (PEG) or with ML 141 (10 µM) 18-20 h prior to infection with *Staphylococcus aureus* at a multiplicity of infection of 30 (2 h). Following infection, extracellular bacteria were removed by incubating with lysostaphin and gentamicin (45 min), antimicrobials with limited mammalian membrane permeability. Antimicrobial-containing media was replenished and incubation extended an additional 24 h. Cells were fixed, stained, and examined by transmission electron microscopy. White arrow indicates mitochondria. Black arrow indicates filopodia. White arrowhead indicates membranous structure surrounding bacteria. Black arrowhead indicates dividing bacteria. Scale bar is 5 µm.

Invasion by *S. aureus* is progressively damaging to the host cell. To examine whether inhibition of invasion and sustained suppression of the intracellular bacterial population limits this damage, host cells were treated with ML 141 or with vehicle control and examined at the ultrastructural level 24 h post-invasion. Following infection, organelles that remained intact within ML 141 treated cells were not detectable within vehicle control treated cells (FIG. 9). At the host cell membrane, filopodia that form in response to infection were not detected in ML 141 treated cells, yet were readily observed in the vehicle control. Bacteria within ML 141 treated cells were located within membranous boundaries. In vehicle control treated cells, bacteria were cytosolic and appeared to be undergoing cellular division. Consistent with the invasion assays, fewer bacteria were observed within ML 141 treated cells.

Small Molecule Inhibition of CDC42 Decreases the Disassembly of Actin Structures During Infection.

In previous work, it was found that during invasion of HUVEC by *S. aureus*, actin stress fibers are disassembled. Here, it was found that ML 141 treatment decreased the disassembly of actin stress fibers during infection (FIG. 8A).

Small Molecule Inhibition of CDC42 Decreases Adhesion Complex Formation and Function.

Figure 10A:
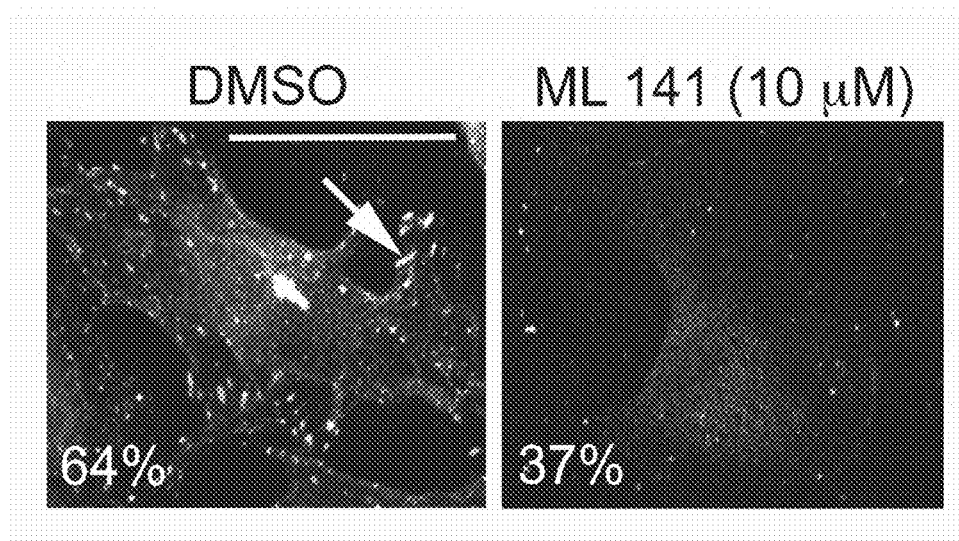
FIG. 10A is an image depicting ML 141 inhibition of CDC42 limiting the formation of adhesion complexes. Human umbilical vein endothelial cells (HUVEC) were incubated (18-20 h) with the vehicle control dimethyl sulfoxide (DMSO) or with ML 141 (10 µM). Pretreated HUVEC were fixed, permeabilized, blocked, and stained with anti-vinculin followed by anti-mouse Alexa Fluor 488. Arrows indicate vinculin-containing complexes. Data are presented as the % of cells where vinculin-containing adhesion complexes were detected. 100-200 cells/treatment were evaluated from randomly selected fields (p<0.001 by $\chi^2$). Scale bar 50 μm.
Figure 10B:
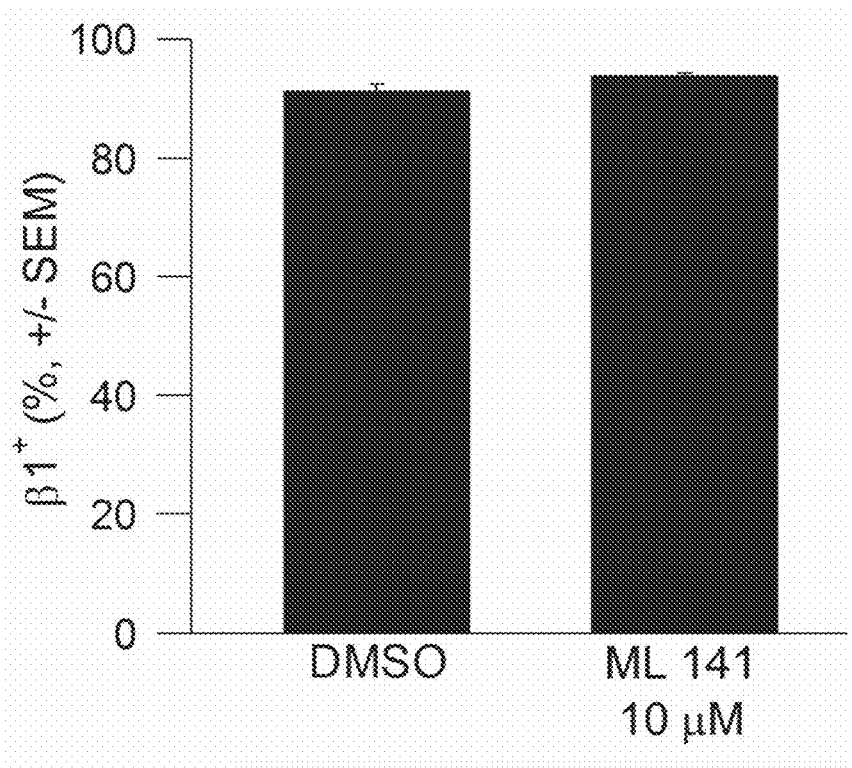
FIG. 10B is a graph illustrating that expression of the β1 integrin subunit remains substantially unchanged in HUVEC incubated with DMSO or ML 141 (10 μM). Pretreated HUVEC were stained with PE conjugated anti-β1 and examined using flow cytometry (no difference between groups was detected, t-test, p>0.05).

*S. aureus* uses adhesion complexes on the host cell membrane to gain host cell entry. These complexes commonly are comprised of cytoskeletal proteins, including actin, tensin, and vinculin, and are organized around the central integrin receptor α5β1. *S. aureus* gains entry at these complexes by attaching to host fibronectin, a ligand of α5β1. As fibronectin binds to the α5β1 receptor and stimulates endocytic uptake, the attached bacteria are taken into the host cell as part of a bacterial/fibronectin/receptor complex. It was previously found that the inhibition of invasion by simvastatin is associated with a decrease in the abundance of these complexes. Here, ML 141 was used to explore whether the decrease is due in part to loss of functional CDC42. ML 141 treatment decreased adhesion complexes from 64% in vehicle control treated cells to 37% in ML 141 treated cells ($p \leq 0.001$ by $\chi^2$, FIG. 10A). The decrease in abundance might also be due to decreased expression of the central organizing integrin, 31. However, no difference in the expression of 31 was detected between treatment groups (FIG. 10B).

Small Molecule Inhibition of CDC42 Decreases Adherence to Fibronectin.

Figure 10C:
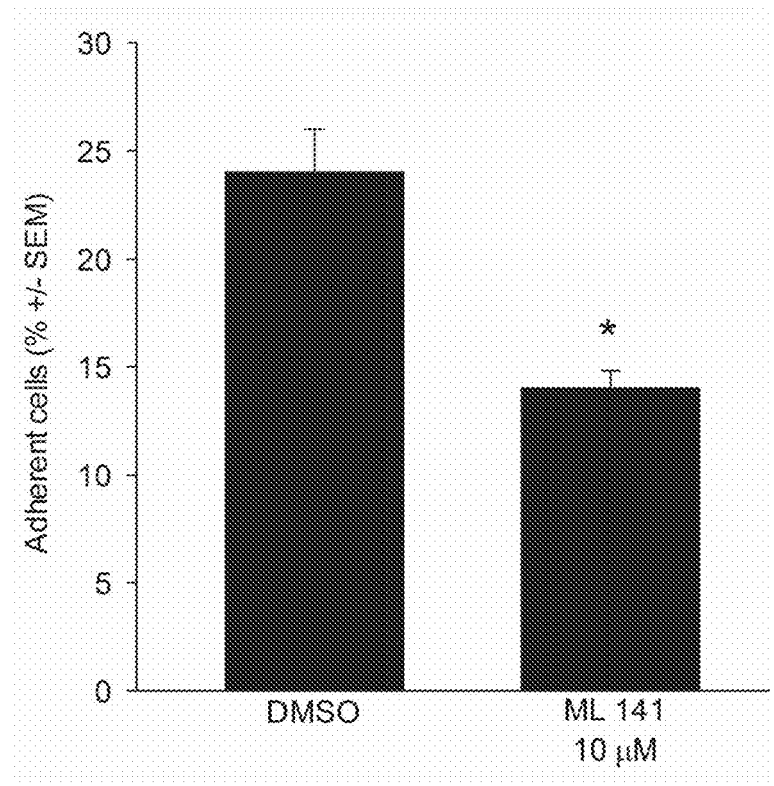
FIG. 10C is a graph illustrating that ML 141 decreases cell adhesion to fibronectin-coated surface. HUVEC were pretreated as in FIGS. 10A and 10B, lifted from culture dishes using cell scrapers, and re-plated (2 h) onto non-tissue culture treated plates coated with fibronectin and blocked with bovine serum albumin. Following extensive washes, cells were recovered using trypsin and counted using an Accuri C6 flow cytometer (*p<0.05 by t-test on log-transformed data pooled from 2 independent experiments, n=8/treatment).

The inhibition of invasion might be due in part to diminished adherence to fibronectin, the ligand of α5β1 used by *S. aureus* for gaining host cell entry. ML 141 treatment decreased adherence of HUVEC to fibronectin-coated plates from 24±4% to 14±2% ($p<0.05$ by Student's t-test, FIG. 10C).

Structural Analogs of ML 141 Limit Host Cell Invasion.

To improve the in vivo potency of ML 141, structural analogs were synthesized. The analogs, designated as the RSM series (structures are available in Table 3), were assessed using the invasion assay. Intracellular bacterial levels were diminished by the analogs in the RSM series (Tables 1 and 2). To verify that the apparent inhibition of invasion was not due to host cell death, cytotoxicity was assessed. RSM 04 and RSM 26 were found to be cytotoxic (Table 4). Cytotoxicity was not detected in response to ML 141 or in response to any additional structural analog (Tables 4 and 5). ML 141 was synthesized originally within a series of potential antimicrobials. To verify that the apparent inhibition of invasion was not due to a loss in numbers of viable bacteria, bactericidal activity was assessed. RSM 26 was found to be bactericidal (Table 6). Bactericidal activity was not detected in response to ML 141 or in response to any additional structural analog (Tables 6 and 7).

Experimental Section 5: ML 141 Inhibition of Cellular Invasion by *Streptococcus* Pyogenes Rationale ML 141 may inhibit invasion by additional clinically important intracellular pathogens, such as *S. pyogenes*, that use fibronectin binding to gain host cell entry. For this, we examined an M+ strain of *Streptococcus pyogenes* (90-226). The M protein is a fibronectin-binding protein of *S. pyogenes* that facilitates invasion.

Materials and Methods

Endothelial Cell Cultures, Bacterial Strains, and Growth Conditions:

Human umbilical vein endothelial cells (HUVEC, EMD Millipore, Billerica, Mass., SCCE001) were cultured in EndoGRO-LS complete media (EMD Millipore, SCME001) and maintained in 75 cm² vented cap flasks (Thermo-Fisher Scientific, Pittsburgh, Pa., 10-126-37) at 37° C./5% $CO_2$. *Streptococcus pyogenes* (90-226, M1+) was cultured in Todd Hewitt broth (THB, Thermo-Fisher Scientific, DF0492-17-6) and grown at 37° C. with no shaking.

Invasion Assay:

Two days prior to infection, *S. pyogenes* were cultured in 5 ml THB 18-24 h from a single colony grown on THB/blood (Cleveland Scientific, Bath, Ohio, SBCIT-100) agar (Moorhead & Company, Rocklin, Calif., gelidium), and 10 μl subcultured 18 h prior to infection. HUVEC were seeded in 24-well plates (Sigma-Aldrich, St. Louis, Mo., CLS3524) that had been coated with Attachment Factor (Life Technologies, Carlsbad, Calif., S006100) for 30 min at 37° C./5% $CO_2$. HUVEC were plated at a density of $1.5 \times 10^5$ cells/well. For infection, *S. pyogenes* were harvested by centrifugation, 37° C./3 min/10,000 RPM, washed, and resuspended in fresh 0.85% saline (NaCl, Thermo-Fisher Scientific, S-271-500). Bacteria were diluted to $4.8 \times 10^8$ colony forming units (CFU)/ml and incubated at 37° C./5% $CO_2$ with HUVEC at multiplicity of infection and for duration indicated in each figure or table. CFU of 90-226 *S. pyogenes* had been determined from a growth curve, fitting an OD600 of 0.5 to $4.8 \times 10^8$ CFU/ml. After infection, each well was washed three times with sterile 1× phosphate buffered saline (PBS, Life Technologies, 20012043) to remove unattached *S. pyogenes*. HUVEC were then incubated at 37° C., 5% $CO_2$ for 45 min in 10% fetal bovine serum (FBS, Atlanta Biologicals, Flowery Branch, Ga., S111S0)/PBS containing 500 μg/ml gentamicin (Sigma-Aldrich, G1272). Following the incubation with gentamicin to remove extracellular bacteria, HUVEC were washed three times with PBS. Sterile distilled ice-cold water (Life Technologies, 15230-162) was added to each well for 5 min at room temperature (RT) to permeabilize the host cells. Serial dilutions of this bacteria-containing water were performed in saline, plated on THB/blood agar, and incubated for 18-20 h at 37° C. The following day, colonies were counted to determine CFU/ml recovered from invasion.

Immunofluorescence:

For actin assessment, HUVEC were seeded at $6 \times 10^5$ cells/ml in 35 mm glass-bottom dishes (MatTek, Ashland, Mass.) that had been coated with Attachment Factor. HUVEC were pretreated with ML 141 or with DMSO and treated with gentamicin as described above. HUVEC were washed three times with PBS and fixed with 4% paraformaldehyde for 30 min, RT. HUVEC were gently washed four times with PBS, permeabilized and blocked with 1% BSA/0.1% Triton (Sigma-Aldrich, T8787). HUVEC were gently washed four times with PBS, probed for actin with Alexa Fluor 488 phalloidin (1:40, Life Technologies, A12379) in PBS (30 min, RT) and washed three more times with PBS. Actin stress fiber assessment was conducted using a Zeiss Axiovert200 microscope equipped with a plan-apochromat 40×/1.2 numerical aperture water immersion lens. A total of 200 HUVEC were assessed for actin stress fiber disassembly from randomly selected fields-of-view. Images were collected using a LSM 5 Pascal scan head.

Results

In response to ML 141 pretreatment (18-20 hours), intracellular bacterial populations were diminished following 2 hours of infection at a MOI of 30 (Table 8). When ML 141 was added at the time of infection at the same MOI of 30, intracellular bacterial populations were not diminished. However, when the MOI was reduced to 0.25, intracellular bacterial populations were lower in the ML 141 treatment group compared to the vehicle control treatment group. Intracellular bacterial populations were lower 24 hours post-infection in the ML 141 treatment group, indicating that the decrease was sustained over time. In order to determine whether ML 141 could limit the progression of infection if administered after the onset of infection, ML 141 was added 1 hour after infection at this same MOI of 0.25, but no reduction of intracellular bacterial populations was detected. However, when the MOI was reduced to 0.0025, intracellular bacterial populations were lower in the ML 141 treatment group compared to the vehicle control treatment group 24 hours post-infection. Taken together, these data suggest that ML 141 inhibits invasion by newly dividing, extracellular bacteria over time.

Figure 12:
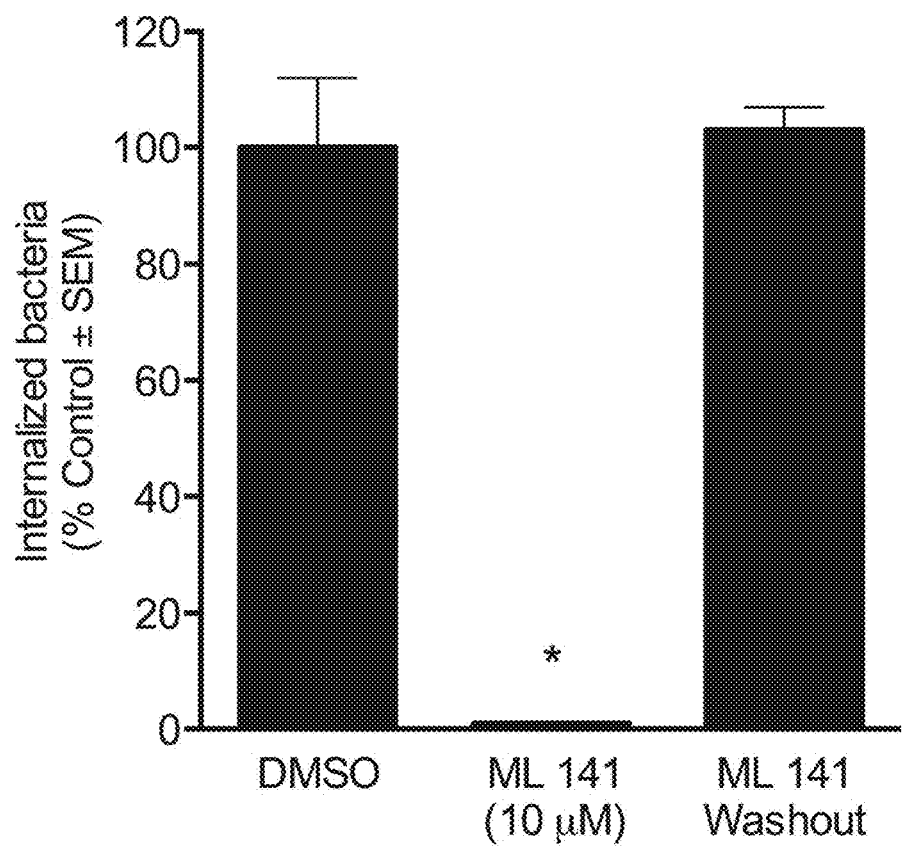
FIG. 12 is a graph illustrating that ML 141 inhibition of cell invasion by *S. pyogenes* is reversible. HUVEC were pretreated with ML 141 (10 μM) or with dimethyl sulfoxide (DMSO) as the vehicle control (1 h). Following pretreatment, ML 141-containing media was removed from the washout samples and replaced with DMSO-containing media for 60 min prior to incubation with *Streptococcus pyogenes* at a multiplicity of infection of 30 (2 h). Extracellular bacteria were removed by gentamicin, an antimicrobial with limited mammalian membrane permeability. Intracellular bacteria were released from HUVEC into the medium by incubation in cold water (5 min). Serial dilutions were incubated (16 h) on Todd Hewitt broth/blood agar plates and colonies enumerated to determine colony forming units (CFU)/ml (*P<0.05 by one-way ANOVA followed by Student-Newman-Keuls post-hoc analysis; n=4/treatment).
Figure 13:
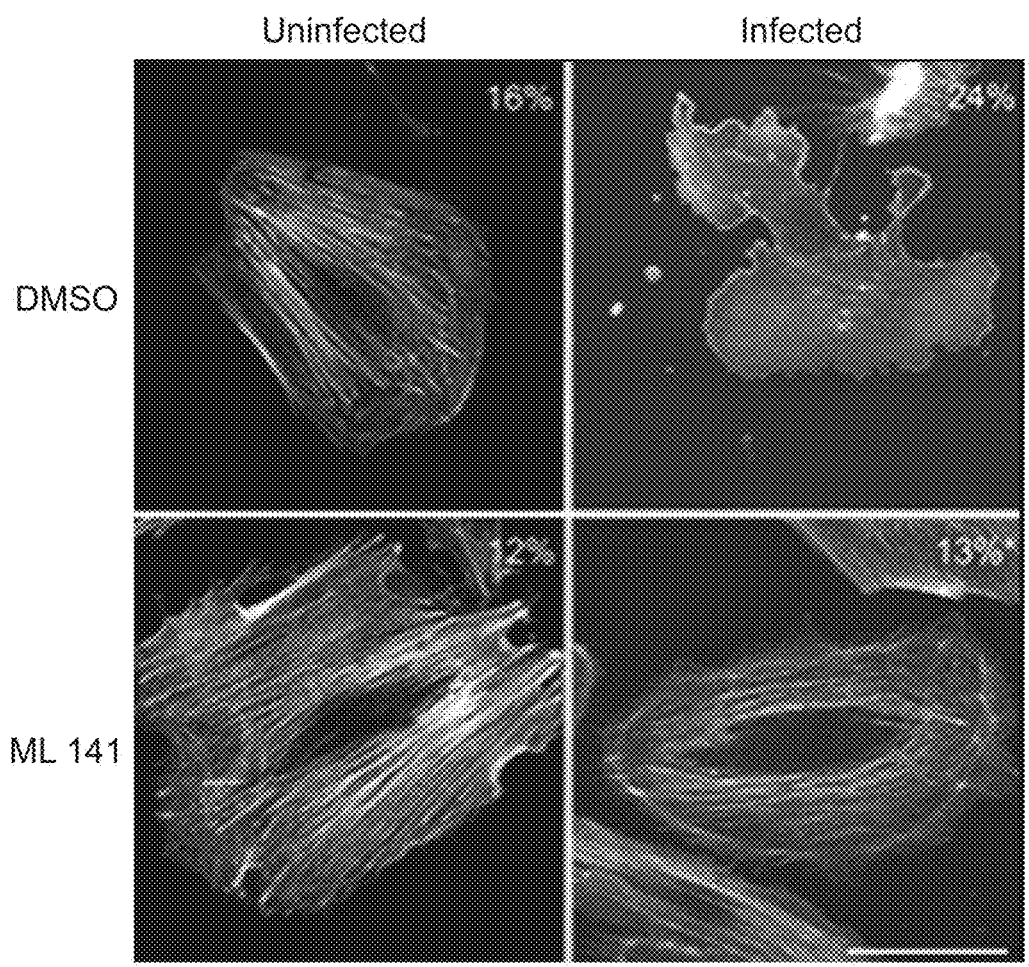
FIG. 13 is an image depicting ML 141 decreasing actin stress fiber depolymerization during infection. HUVEC were incubated with vehicle control dimethyl sulfoxide (DMSO) or with ML 141 (10 μM) 18-20 h prior to infection with *Streptococcus pyogenes* at a multiplicity of infection of 30 (2 h). Actin was detected using Alexa Fluor 488 phalloidin. Data are presented as the percentage of HUVEC with no detectable actin stress fibers. 100-200 cells/treatment were evaluated from randomly selected fields. Scale bar is 50 μm (P<0.05 by $\chi^2$ test of association).
Figure 14A:
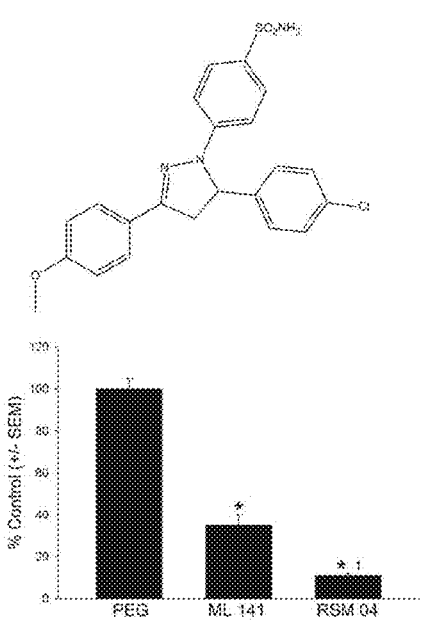
FIG. 14A is a depiction of the chemical structure of the RSM 04 structural analog of ML 141 and a chart indicating its ability to inhibit *Staphylococcus aureus* invasion of human umbilical vein endothelial cells as compared to ML141 and a PEG control.
Figure 14B:
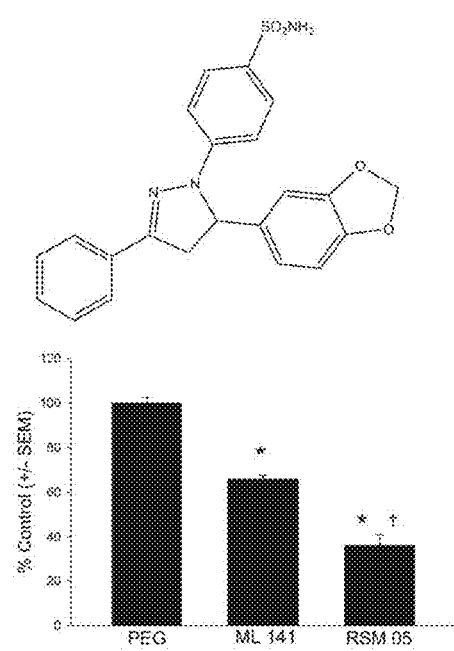
FIG. 14B is a depiction of the chemical structure of the RSM 05 structural analog of ML 141 and a chart indicating its ability to inhibit *Staphylococcus aureus* invasion of human umbilical vein endothelial cells as compared to ML141 and a PEG control.
Figures 14G, 14H:
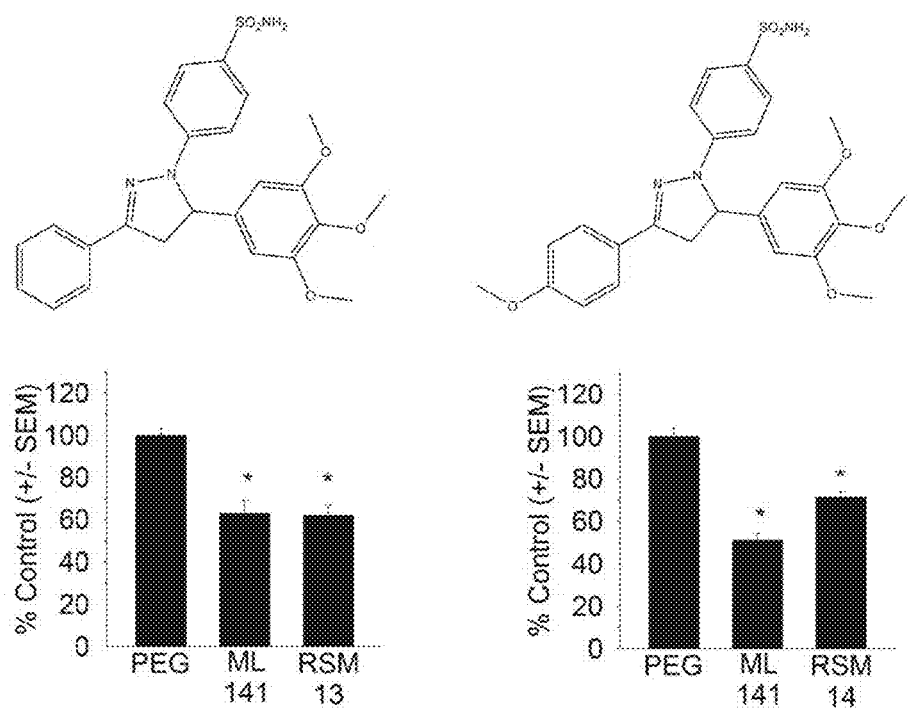
FIG. 14G is a depiction of the chemical structure of the RSM 13 structural analog of ML 141 and a chart indicating its ability to inhibit *Staphylococcus aureus* invasion of human umbilical vein endothelial cells as compared to ML141 and a PEG control.
FIG. 14H is a depiction of the chemical structure of the RSM 14 structural analog of ML 141 and a chart indicating its ability to inhibit *Staphylococcus aureus* invasion of human umbilical vein endothelial cells as compared to ML141 and a PEG control.
Figure 14M:
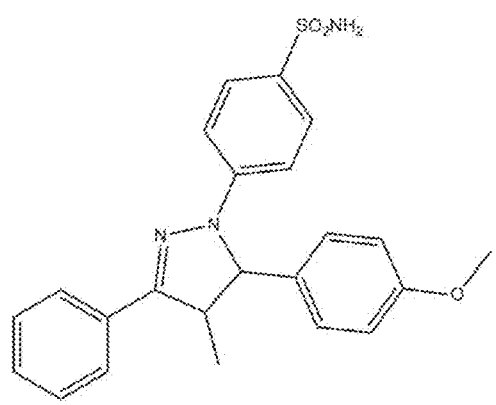
FIG. 14M is a depiction of the chemical structure of the RSM 19 structural analog of ML 141 and a chart indicating its ability to inhibit *Staphylococcus aureus* invasion of human umbilical vein endothelial cells as compared to ML141 and a PEG control.
Figure 14M:
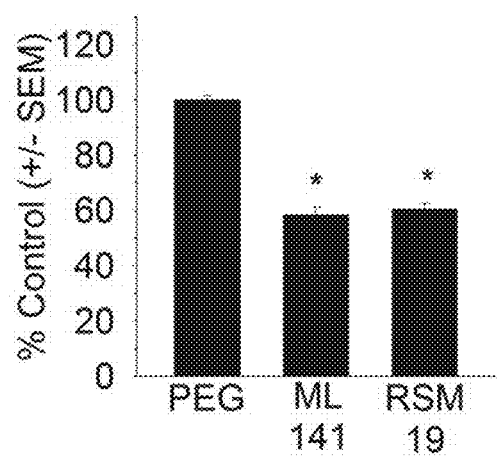
Figure 15A:
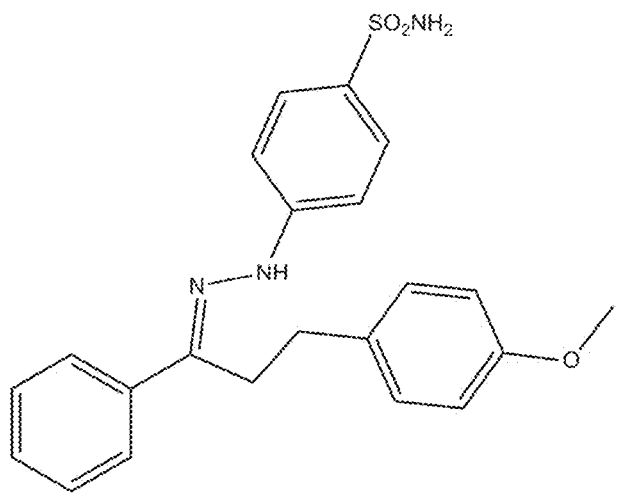
FIG. 15A is a depiction of the chemical structure of the RSM 27 structural analog of ML 141.
Figure 15B:
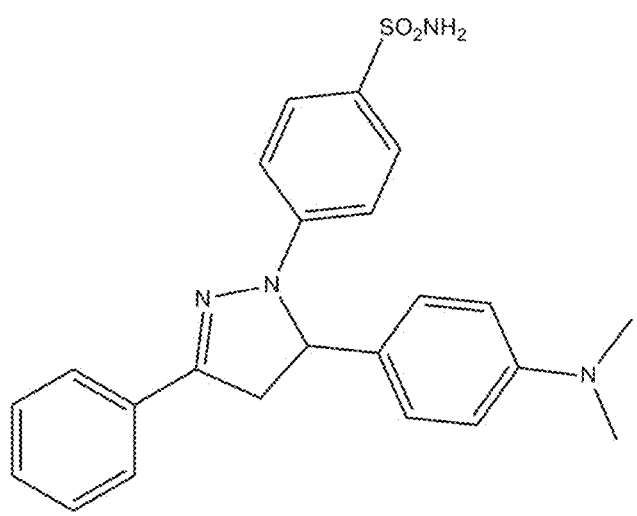
FIG. 15B is a depiction of the chemical structure of the RSM 28 structural analog of ML 141.
Figure 15C:
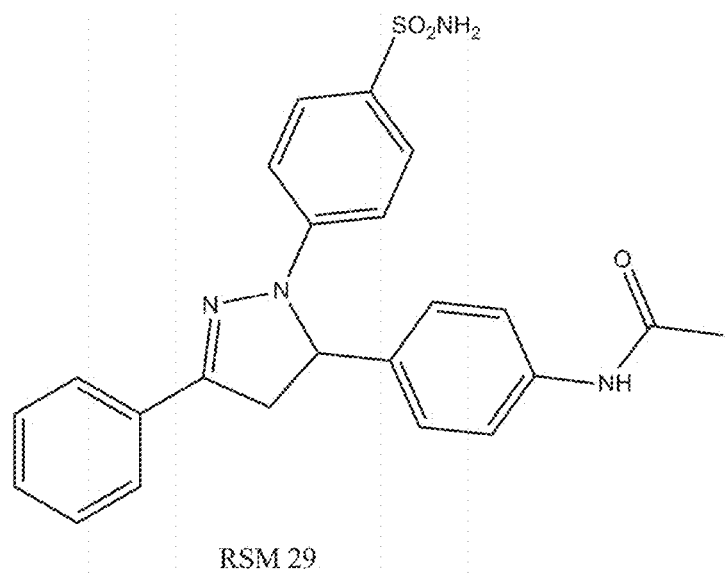
FIG. 15C is a depiction of the chemical structure of the RSM 29 structural analog of ML 141.
Figure 15D:
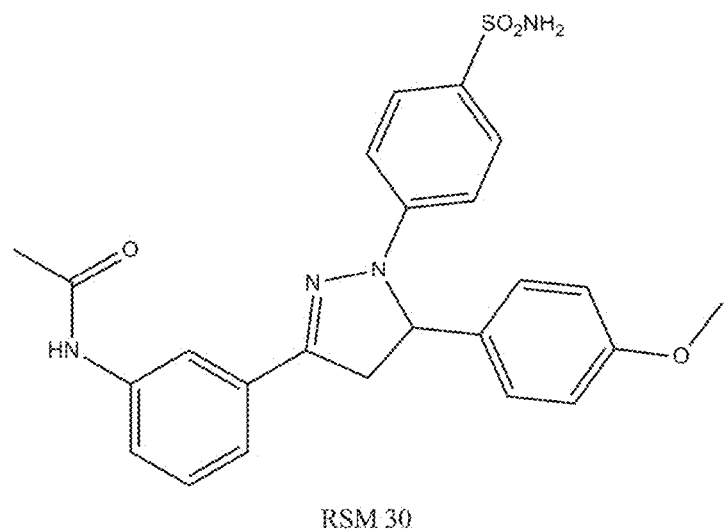
FIG. 15D is a depiction of the chemical structure of the RSM 30 structural analog of ML 141.
Figure 15E:
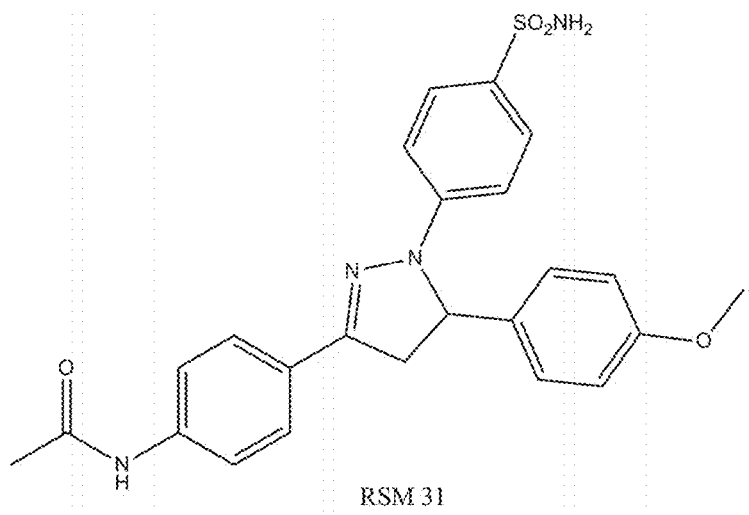
FIG. 15E is a depiction of the chemical structure of the RSM 31 structural analog of ML 141.
Figure 15F:
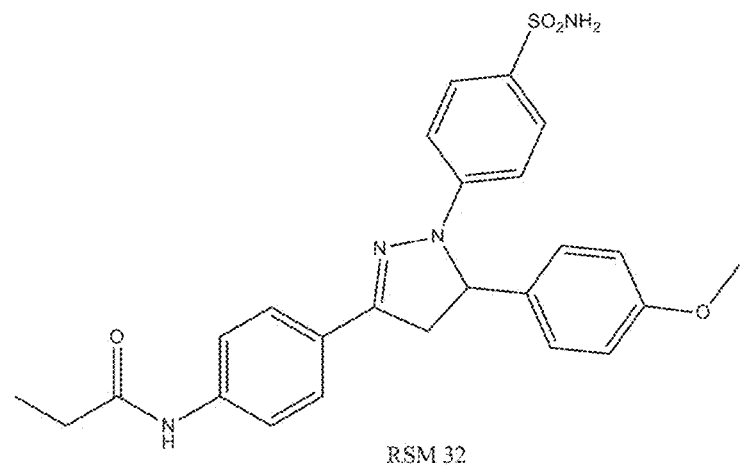
FIG. 15F is a depiction of the chemical structure of the RSM 32 structural analog of ML 141.
Figure 15G:
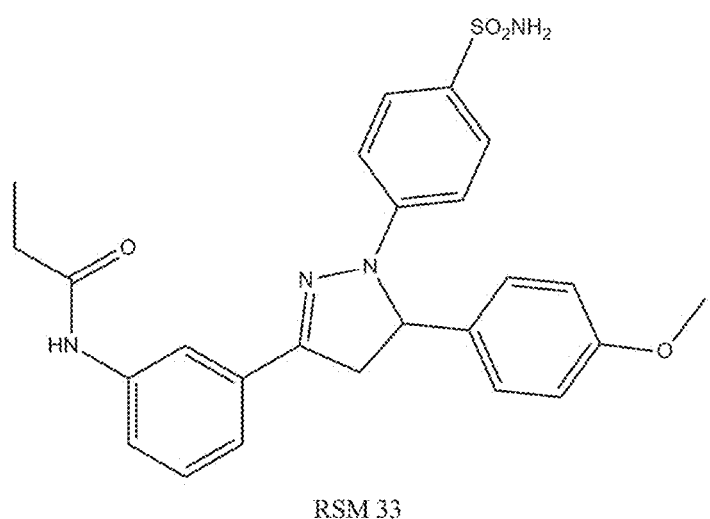
FIG. 15G is a depiction of the chemical structure of the RSM 33 structural analog of ML 141.

Similar to the inhibition of *S. aureus* invasion, inhibition of *S. pyogenes* invasion by ML 141 was reversible (FIG. 12) and was associated with less reordering of actin stress fibers (FIG. 13).

TABLE 8

Assessment of effect of ML 141 on *Streptococcus pyogenes* invasion. HUVEC were treated with ML 141 (10 µM) or with dimethyl sulfoxide as the vehicle control and incubated with *Streptococcus pyogenes* at the MOI indicated. Extracellular bacteria were removed by gentamicin, an antimicrobial with limited mammalian membrane permeability. Intracellular bacteria were released from HUVEC into the medium by incubation in cold water (5 min). Serial dilutions were incubated (16 h) on Todd Hewitt broth/blood agar plates and colonies enumerated to determine colony forming units (CFU)/ml. Data are % inhibition relative to control ± SEM (*P < 0.05 by Student's t-test; n = 3-5/treatment).

| Compound Addition | Duration of Infection | MOI | % Inhibition (± SEM) |
|---|---|---|---|
| 18-20 hours pre-infection | 2 h | 30 | 96 ± 4%* |
| Time of infection | 2 h | 30 | No difference |
| Time of infection | 2 h | 0.25 | 81 ± 7%* |
| Time of infection | 2 h | 0.25 | 62 ± 10%* |
| 1 hour post-infection | 2 h | 0.25 | No difference |
| 1 hour post-infection | 2 h | 0.0025 | 92 ± 6%* |

Pre-treatment of host cells with ML 141 or its analogs could limit infection by clinically important pathogens reliant on fibronectin-binding for invasion by inhibition of CDC42. Such fibronectin-reliant intracellular pathogens include *Coxiella burnetii, Chlamydia, Legionella,* and *Bartonella,* which use fibronectin-binding to invade endocardial tissue during infective endocarditis, *Mycobacterium leprae,* a causative agent of leprosy, and by *Neisseria gonorrhoeae,* the causative agent of gonorrhea.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

The invention claimed is:

1. A method of suppressing bacterial infection comprising:
administering ML 141 or its analogs to cells infected by *Staphylococcus*,
where the analogs are defined by the following structures:

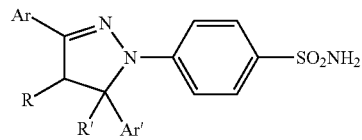

where
Ar is phenyl, acetamidophenyl (-Ph-NH—CO-Me), or propanamidophenyl (-Ph-NH—CO-Et), R is hydrogen, R' is hydrogen, and Ar' is methoxyphenyl (-Ph-O-Me), acetamidophenyl (-Ph-NH—CO-Me), or dimethylaminophenyl (-Ph-N-Me$_2$); and

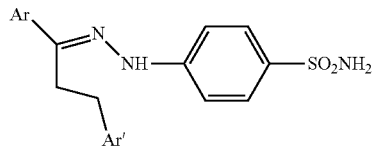

where Ar is phenyl and Ar' is methoxyphenyl (-Ph-O-Me).

2. The method of claim 1 wherein said bacterial infection is from *Staphylococcus aureus*.

3. The method of claim 1 wherein administering includes providing ML 141 or its analogs adjacent to the cells.

4. The method of claim 1 wherein administering includes testing at least one analog on the cells.

5. The method of claim 1 wherein suppressing bacterial infection includes suppressing initial bacterial infection.

6. The method of claim 1 wherein suppressing bacterial infection includes suppressing persistent bacterial infection.

7. The method of claim 6 wherein administering includes providing approximately 1 µM of ML 141 or its analogs.

8. The method of claim 6 wherein administering includes providing approximately 10 µM of ML 141 or its analogs.

9. The method of claim 1 wherein administering occurs subsequent to the onset of bacterial infection.

10. The method of claim 1 wherein the cells are animal cells.

11. The method of claim 1 wherein the cells are human cells.

12. The method of claim 1 wherein the cells express CDC42.

13. A method of suppressing bacterial infection, comprising:
providing a chemical defined by the following structures:

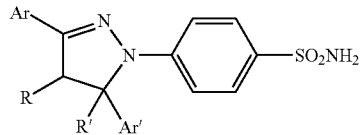

where
Ar is phenyl, acetamidophenyl (-Ph-NH—CO-Me), or propanamidophenyl (-Ph-NH—CO-Et), R is hydrogen, R' is hydrogen, and Ar' is methoxyphenyl (-Ph-O-Me), acetamidophenyl (-Ph-NH—CO-Me), or dimethylaminophenyl (-Ph-N-Me$_2$); and

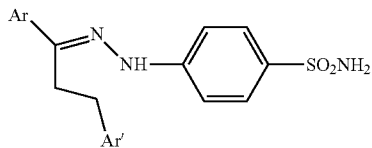

where Ar is phenyl and Ar' is methoxyphenyl (-Ph-O-Me); and
providing the chemical to cells infected by *Staphylococcus*.

14. The method of claim 13 further comprising providing a pharmaceutically accepted solvent or delivery vehicle selected from the group consisting of polyethylene glycol (PEG), dimethyl sulfoxide, ethanol, and combinations thereof.

15. The method of claim 14 wherein the solvent or delivery vehicle is polyethylene glycol.

16. A method of suppressing bacterial infection comprising:
administering ML 141 or its analogs to a patient infected by bacteria of the genus *Staphylococcus*,
where the analogs are defined by the following structures:

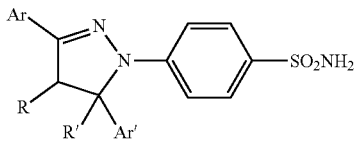

where
Ar is phenyl, acetamidophenyl (-Ph-NH—CO-Me), or propanamidophenyl (-Ph-NH—CO-Et), R is hydrogen, R' is hydrogen, and Ar' is methoxyphenyl (-Ph-O-Me), acetamidophenyl (-Ph-NH—CO-Me), or dimethylaminophenyl (-Ph-N-Me$_2$); and

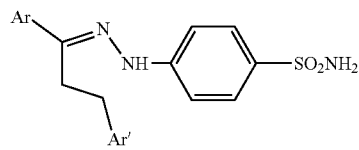

where Ar is phenyl and Ar' is methoxyphenyl (-Ph-O-Me).

* * * * *